United States Patent
Wang

(10) Patent No.: US 10,436,644 B2
(45) Date of Patent: Oct. 8, 2019

(54) MITIGATING MENISCUS EFFECTS IN VERTICALLY ORIENTED CIRCULAR DICHROISM SPECTROMETERY

(71) Applicant: Hinds Instruments, Inc., Hillsboro, OR (US)

(72) Inventor: Baoliang Wang, Hillsboro, OR (US)

(*) Notice: Subject to any disclaimer, the term of this patent is extended or adjusted under 35 U.S.C. 154(b) by 0 days.

(21) Appl. No.: 15/765,698

(22) PCT Filed: Oct. 6, 2016

(86) PCT No.: PCT/US2016/055787
§ 371 (c)(1),
(2) Date: Apr. 3, 2018

(87) PCT Pub. No.: WO2017/062644
PCT Pub. Date: Apr. 13, 2017

(65) Prior Publication Data
US 2018/0283948 A1    Oct. 4, 2018

Related U.S. Application Data

(60) Provisional application No. 62/238,115, filed on Oct. 6, 2015.

(51) Int. Cl.
*G01J 3/447*    (2006.01)
*G01N 21/19*    (2006.01)
(Continued)

(52) U.S. Cl.
CPC ............. *G01J 3/447* (2013.01); *G01J 3/0205* (2013.01); *G01J 3/0224* (2013.01); *G01J 4/04* (2013.01);
(Continued)

(58) Field of Classification Search
CPC ...... G01J 3/02; G01J 3/447; G01J 3/18; G01J 3/42; G01N 21/211
(Continued)

(56) References Cited

U.S. PATENT DOCUMENTS

| 4,730,921 A | 3/1988 | Klein et al. |
| 6,046,448 A | 4/2000 | Sato et al. |

(Continued)

FOREIGN PATENT DOCUMENTS

WO    WO 2013/138090    9/2013

OTHER PUBLICATIONS

International Search Report and Written Opinion dated Jan. 6, 2017, from International Patent Application No. PCT/US2016/055787, 13 pp.

*Primary Examiner* — Md M Rahman
(74) *Attorney, Agent, or Firm* — Klarquist Sparkman, LLP

(57) ABSTRACT

Example embodiments of methods, apparatus, and systems for measuring polarimetric parameters using spectroscopy are disclosed herein. Particular embodiments concern circular dichroism (CD) spectrometers that use a vertically aligned beam. In such embodiments, the solution being analyzed may have a top surface that forms a convex or concave meniscus, creating a surface through which the measuring beam passes that may refract the beam in undesirable ways. Accordingly, particular embodiments of the disclosed technology include one or more meniscus-compensating (meniscus-effect-reducing) components or subsystems. These components and/or subsystems can be used alone or in combination with one another to reduce the undesirable refractive effects caused by the meniscus at the solution's surface, thereby improving the resulting quality of (Continued)

the spectroscopy measurement and potentially improving the speed with which CD spectroscopy can be performed.

16 Claims, 19 Drawing Sheets

(51) Int. Cl.
 *G01N 21/21* (2006.01)
 *G01N 21/25* (2006.01)
 *G01J 4/04* (2006.01)
 *G01J 3/02* (2006.01)
 *G01J 4/00* (2006.01)

(52) U.S. Cl.
 CPC .............. *G01N 21/19* (2013.01); *G01N 21/21* (2013.01); *G01N 21/253* (2013.01); *G01J 2004/001* (2013.01); *G01N 2021/216* (2013.01)

(58) Field of Classification Search
 USPC ......................................................... 356/327
 See application file for complete search history.

(56) References Cited

U.S. PATENT DOCUMENTS

| | | |
|---|---|---|
| 6,268,914 B1 | 7/2001 | Wang |
| 6,552,340 B1 | 4/2003 | Krivanek et al. |
| 7,301,632 B2 | 11/2007 | Hug |
| 2008/0309933 A1 | 12/2008 | Gould et al. |

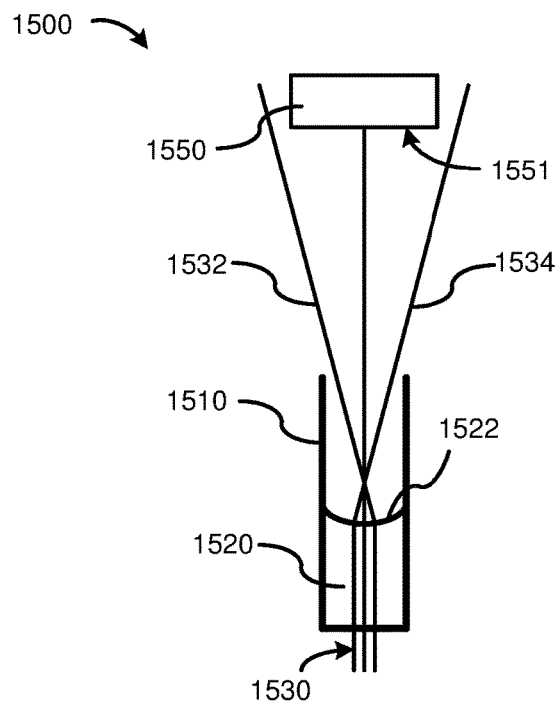
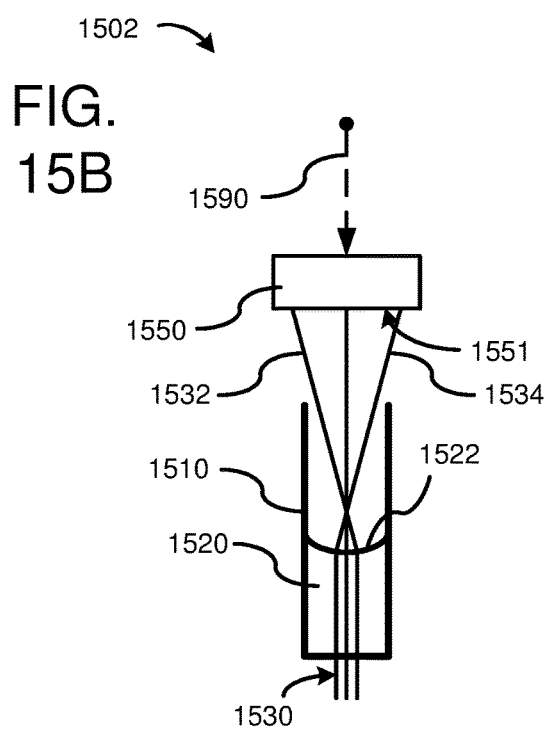
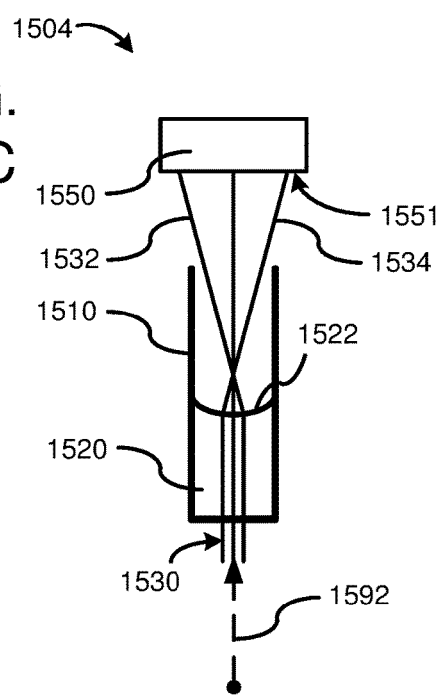
FIG. 15A
FIG. 15B
FIG. 15C

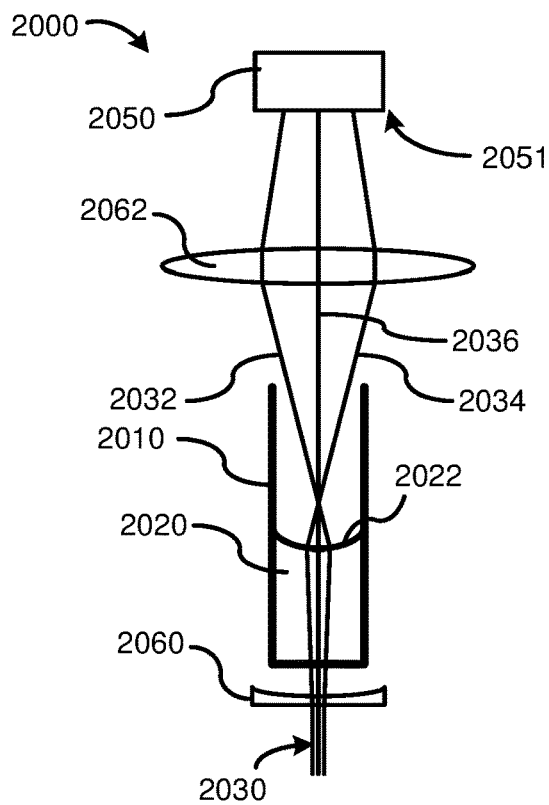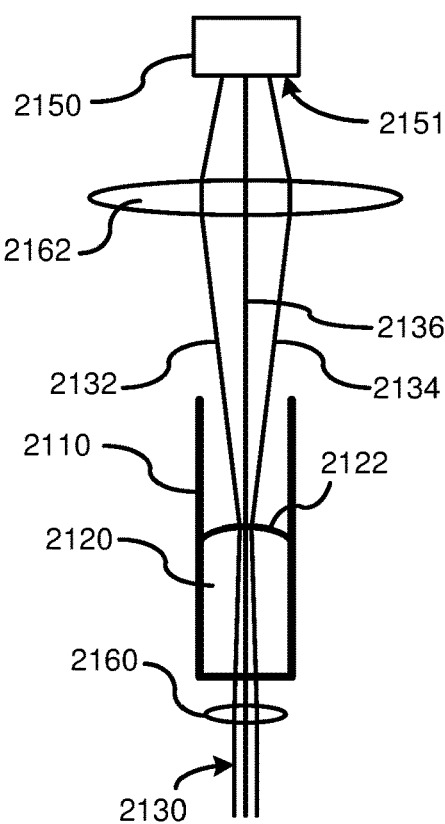
FIG. 20
FIG. 21

MITIGATING MENISCUS EFFECTS IN VERTICALLY ORIENTED CIRCULAR DICHROISM SPECTROMETERY

CROSS REFERENCE TO RELATED APPLICATION

This application is the U.S. National Stage of International Application No. PCT/US2016/055787, entitled "MITIGATING MENISCUS EFFECTS IN VERTICALLY ORIENTED CIRCULAR DICHROISM SPECTROMETERY," filed Oct. 6, 2016, which was published in English under PCT Article 21(2), which in turn claims the benefit of U.S. Provisional Application No. 62/238,115, entitled "MITIGATING MENISCUS EFFECTS IN VERTICALLY ORIENTED CIRCULAR DICHROISM SPECTROMETERY" and filed on Oct. 6, 2015, which is hereby incorporated herein by reference in its entirety.

FIELD

This application relates generally to the field of measuring polarimetric parameters using circular dichroism spectroscopy.

SUMMARY

Disclosed below are representative embodiments of methods, apparatus, and systems for measuring polarimetric parameters using spectroscopy. Particular embodiments concern circular dichroism (CD) spectrometers that use a vertically aligned beam. In such embodiments, the solution being analyzed may have a top surface that forms a convex or concave meniscus, creating a surface through which the measuring beam passes that may refract the beam in undesirable ways. Accordingly, particular embodiments of the disclosed technology include one or more meniscus-compensating (meniscus-effect-reducing) components or subsystems. These components and/or subsystems can be used alone or in combination with one another to reduce the undesirable refractive effects caused by the meniscus at the solution's surface, thereby improving the resulting quality of the spectroscopy measurement and potentially improving the speed with which CD spectroscopy can be performed.

The disclosed methods, apparatus, and systems should not be construed as limiting in any way. Instead, the present disclosure is directed toward all novel and/or nonobvious features and aspects of the various disclosed embodiments, alone or in various combinations and subcombinations with one another.

BRIEF DESCRIPTION OF THE DRAWINGS

FIGS. 15A-15C are block diagrams illustrating mechanical techniques for reducing meniscus effects in systems having a light source located below the solution being measured.

FIGS. 16-21 are block diagrams illustrating optical components for reducing meniscus effects in systems having a light source located below the solution being measured.

DETAILED DESCRIPTION

I. General Considerations

Figure 1:
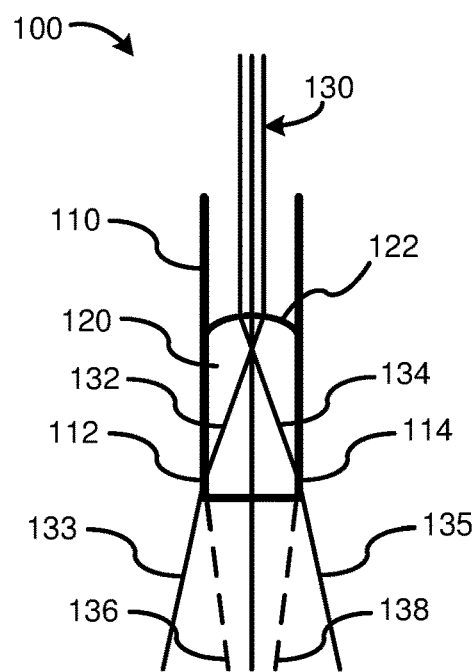
FIGS. 1-4 are block diagrams that illustrate several examples of a meniscus of a solution in a sample vessel or a well of a well plate that creates a potentially deleterious meniscus effect.

Disclosed below are representative embodiments of methods, apparatus, and systems for measuring polarimetric parameters using spectroscopy. Particular embodiments concern circular dichroism (CD) spectrometers that use a vertically aligned beam.

The disclosed methods, apparatus, and systems should not be construed as limiting in any way. Instead, the present disclosure is directed toward all novel and nonobvious features and aspects of the various disclosed embodiments, alone and in various combinations and subcombinations with one another. Furthermore, any features or aspects of the disclosed embodiments can be used in various combinations and subcombinations with one another. For example, one or more method acts from one embodiment can be used with one or more method acts from another embodiment and vice versa. The disclosed methods, apparatus, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods or systems. Additionally, as used herein, the term "and/or" means any one item or combination of items in the phrase.

II. Example Embodiments

A. Introduction

Polarimetric parameters, such as circular dichroism, optical rotation, linear birefringence, or linear diattenuation can be measured spectroscopically. A transmissive-type spectrometer directs light through a substance to be analyzed, and the light propagating from the substance is received on a detector and analyzed to determine one or more of the polarimetric parameters pertaining to the substance.

A spectrometer that is dedicated to the measure of circular dichroism (CD) is often referred to as a CD spectrometer, and can be used for analyzing chiral substances in chemistry, biochemistry, and the pharmaceutical industry. Circular dichroism refers to the differential absorption of left- and right-circularly polarized light (e.g., $\Delta A = A_L - A_R$, where $\Delta A$ (Differential Absorbance) is the difference between absorbance of left circularly polarized light ($A_L$) and right circularly polarized light ($A_R$)). Further, circular dichroism is wavelength dependent. Thus, in certain embodiments of the disclosed technology, multiple different CD measurements are obtained at a plurality of different wavelengths or wavelength bands. Chiral or optically active substances exhibit CD.

A CD spectrometer typically measures the CD of a substance over a range of wavelengths in the ultraviolet, visible, and infrared (UV-Vis-IR) spectral region. Such CD spectrometers are typically based on light source instrumentation that requires sequentially scanning one narrow band of wavelengths at a time across the entire spectrum of interest. This sequential scanning technique may be carried out by a monochromator, for example, that is associated with the light source.

In combinatorial chemistry, or similar processes, various combinations of reagents and catalysts are reacted in multiple-well well plates (also referred to as microplates). For example, a 96-well well plate contains 96 wells in a 12×8 array. Each well contains a specific combination of the reagent and catalyst. Thus, 96 wells contain 96 distinct combinations for analysis.

In a typical CD spectrometer system, the content in each well is usually transferred from the well to a sample cell within a sample chamber located in the CD spectrometer system. CD data is then collected for one sequentially-scanned narrow band of wavelengths at a time for the content of each particular well. Further, the measuring light beam that is transmitted through the sample chamber in all commercial, traditional CD spectrometers is horizontally oriented. The sample cell in this type of CD spectrometer needs to be thoroughly cleaned after each of the 96 wells is handled. This is a time consuming process, and often a major bottleneck in drug discovery. Further, the process of transferring the content of each well into a sample cell potentially introduces contaminants that may affect the resulting measurements.

Embodiments of the disclosed technology comprise systems that are capable of performing rapid spectroscopic measurements of polarimetric parameters. Particular embodiments greatly increase the operational speed of CD by directly analyzing CD in multi-well plates using a vertically oriented beam. In certain embodiments, for example, the source light beam is directed vertically through each one of the wells while the solution remains in the well rather than, as with other systems, sequentially transporting the contents of each well into a separate sample cell of the device for analysis.

In particular implementations, the well plate can be mounted in a holder for controlled motion (e.g., in the horizontal plane, in the vertical plane, or both). The motion of the well plate can be automatically controlled by a computer.

As noted, in particular embodiments, the beam is vertically oriented and directed directly into and through the well (and hence the contained sample). In other words, the beam is vertically oriented and directed between the vertical walls that define each well in the microplate. As more fully explained below, the source of the beam may be either above the sample (e.g., above the well of the well plate) or below the sample (e.g., below the well of the well plate).

When a solution of certain chemicals and certain solvents is introduced to a particular well in a well plate, however, the top surface of the solution is often concave or convex due to the surface tension properties of the solution contained in the well and/or the well wall material. This curved surface of the solution in the well is referred to as a "meniscus". Because the index of refraction of a common sample in a solution is significantly higher than that of air, the curved top surface acts like a lens to refract the measuring light beam. This refraction can alter the shape and direction of the beam in a manner that results in a significant degradation in the quality of the spectroscopic measurement. For instance, the refraction caused by the meniscus can cause the surface area of the beam incident on the active surface of the measuring subsystem or device (e.g., a photomultiplier tube (PMT), avalanche photodiode (APD), or charge-coupled device (CCD) along with any other components used in the measuring system, such as a filter or dispersive element) to be significantly less than what would occur in the absence of the meniscus. Consequently, the signal-to-noise ratio can be negatively affected, reducing the quality of the measurement and the speed with which effective measurements can be obtained. In some cases, the meniscus prevents useful spectroscopic measurements from being taken at all. The refracting effect caused by the meniscus of the solution is referred to as the "meniscus effect".

FIGS. 1-4 are block diagrams that illustrate several examples of a meniscus of a solution in a well of a well plate creating a potentially deleterious meniscus effect. With each case, if the detector with a finite active area is placed at a large enough distance from the top surface of the solution in a well, only a small portion of the measuring light beam will reach the detector, thus decreasing the signal level and adversely affecting the signal-to-noise ratio. This problem becomes even more pronounced when the well diameter becomes smaller. For example, this problem is more significant in well plates with wells having smaller diameters, such as well plates having 3 mm wells (e.g., as in a 24×16 well array, where the diameter of a well is approximately 3 mm, or a 48×32 well array, where the diameter is approximately 1 mm). In such small diameter well plates, the potential for the beam interfacing with the vertical side walls of the wells, and thus creating deleterious and potentially unknown reflective and refractive beam components, is increased.

More specifically, FIG. 1 is a block diagram 100 showing a cross-sectional side view of a well 110 containing a solution 120 and having a vertically oriented beam 130 incident on a top surface of the solution 120. In FIG. 1 the beam originates from above the well 110. Further, the top surface of the solution 120 forms a convex meniscus 122, which acts as a convergent (focusing) lens for the incident beam 130. In FIG. 1, the curvature of the meniscus 122 is large enough such that the incident beam has an angle of refraction that causes the focal point to be within an upper half of the solution 120 and to subsequently have beam edges 132, 134 that are incident upon the vertical walls of the well 110 (as shown at points 112, 114). The interference by the vertical walls of the well 110 can cause the beam to partially refract (as illustrated by beam edges 133, 135), partially reflect (as illustrated by reflected beam edges 136, 138), partially scatter in many directions (not shown), and thus generally affect the quality and accuracy of the resulting measurements (e.g., because the partial refraction, reflection, and scattering all introduce to the beam different polarization information than the sample has). Further, the angle of refraction caused by the meniscus 122 can cause a significant reduction in the surface area of the propagating beam that is actually measured at the active detection region of the detection subsystem (e.g., by causing a significant portion of the transmitted beam to not be incident with the active measurement surface of the detection subsystem), further degrading the quality of the measurement.

Figure 2:
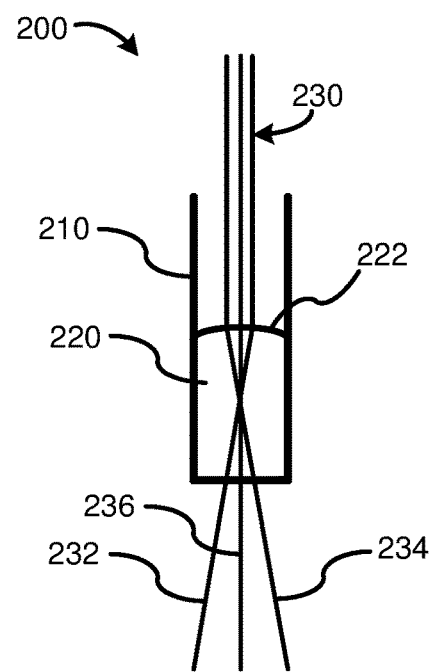

FIG. 2 is a block diagram 200 showing another cross-sectional side view of a well 210 containing a solution 220 and having a vertically oriented beam 230 incident on a top surface of the solution 220. In FIG. 2 the beam originates from above the well 210. Further, the top surface of the solution 220 forms a convex meniscus 222, which acts as a convergent lens for the incident beam 230. In FIG. 2, the curvature of the meniscus 222 is less than in FIG. 1 but still large enough such that the incident beam 230 refracts to create an unintended focal point (either in the solution 220 or out of the solution) and to subsequently have beam edges 232, 234 that diverge from a beam center point 236. The angle of refraction caused by the meniscus 222 and the resulting divergence of the beam (as illustrated by beam portions 236, 238) can cause a significant reduction in the surface area of the propagating beam that is actually measured at a measurement sensor (e.g., an active measurement surface of a detection subsystem) located distally from the beam source.

Figure 3:
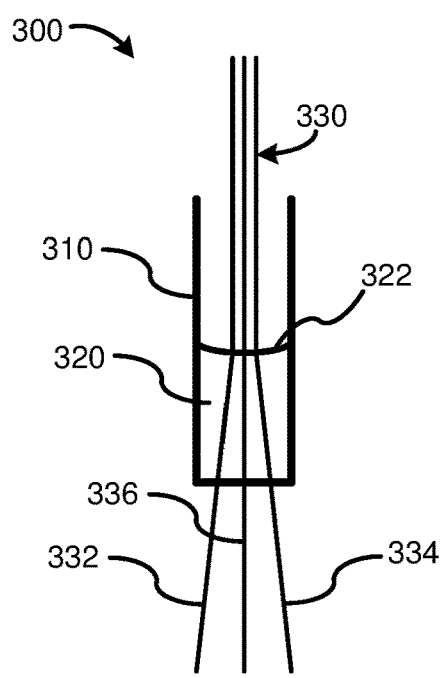

FIG. 3 is a block diagram 300 showing another cross-sectional side view of a well 310 containing a solution 320 and having a vertically oriented beam 330 incident on a top surface of the solution 320. In FIG. 3 the beam originates from above the well 310. Further, the top surface of the solution 320 forms a concave meniscus 322, which acts as a divergent (defocusing) lens for the incident beam 330. In FIG. 3, the curvature of the meniscus 322 refracts the incident beam such that its beam edges 332, 334 diverge from a center point 336 upon passing through the meniscus. The angle of refraction caused by the meniscus 322 and the resulting divergence of the beam (as illustrated by beam edges 332, 334) can cause a significant reduction in the surface area of the propagating beam that is actually measured at a measurement sensor (e.g., an active measurement surface of a detection subsystem) located distally from the beam source.

Figure 4:
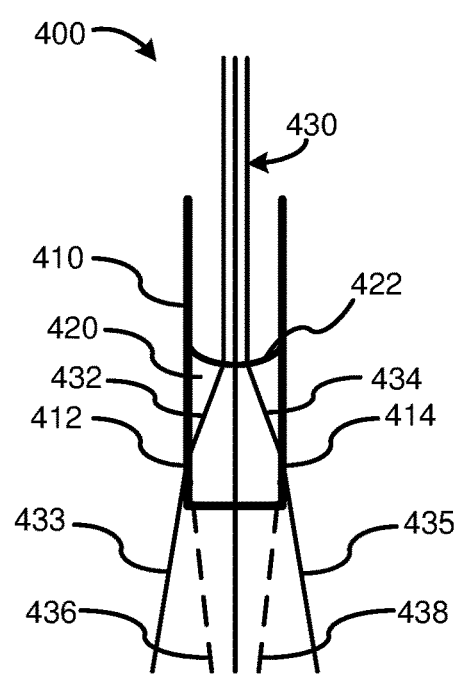

FIG. 4 is a block diagram 400 showing a cross-sectional side view of a well 410 containing a solution 420 and having a vertically oriented beam 430 incident on a top surface of the solution 420. In FIG. 4 the beam originates from above the well 410. Further, the top surface of the solution 420 forms a concave meniscus 422, which acts as a divergent lens for the incident beam 430. In FIG. 4, the curvature of the meniscus 422 is larger than in FIG. 3 and large enough such that the incident beam has an angle of refraction that causes the beam edges 432, 434 to be incident with the vertical walls of the well 410 (as shown at points 412, 414). The interference by the vertical walls of the well 410 can cause the beam to partially refract (as illustrated by beam edges 433, 435), partially reflect (as illustrated by reflected beam portions 436, 438), partially scatter in many directions (not shown), and thus generally affect the quality and accuracy of the resulting measurements (e.g., because the partial refraction, reflection, and scattering all introduce to the beam different polarization information than the sample has). Further, the angle of refraction caused by the meniscus 422 can cause a significant reduction in the surface area of the propagating beam that is actually measured at the active detection region of the detection subsystem (e.g., by causing a significant portion of the transmitted beam to not be incident with the active measurement surface of the detection subsystem), further degrading the quality of the measurement.

B. Vertically Oriented CD Systems with Meniscus-Mitigation Components

To help address these meniscus effects, one or more meniscus mitigation components/approaches can be implemented into a CD spectroscopy system. Any one or more of these approaches and/or systems can be implemented alone or together in any combination with one another. In general, the disclosed meniscus mitigation approaches operate to improve the signal-to-noise ratio of the measurement (e.g., by increasing the surface area of the beam incident on the measurement device). For example, in particular implementations, the signal-to-noise ratio is increased to 3:1 or greater. In certain instances, the disclosed approaches can also serve to prevent the beam from interfacing with the vertical side walls of a well during a measurement, thereby improving the measurement accuracy as well as the signal-to-noise ratio.

Figure 5:
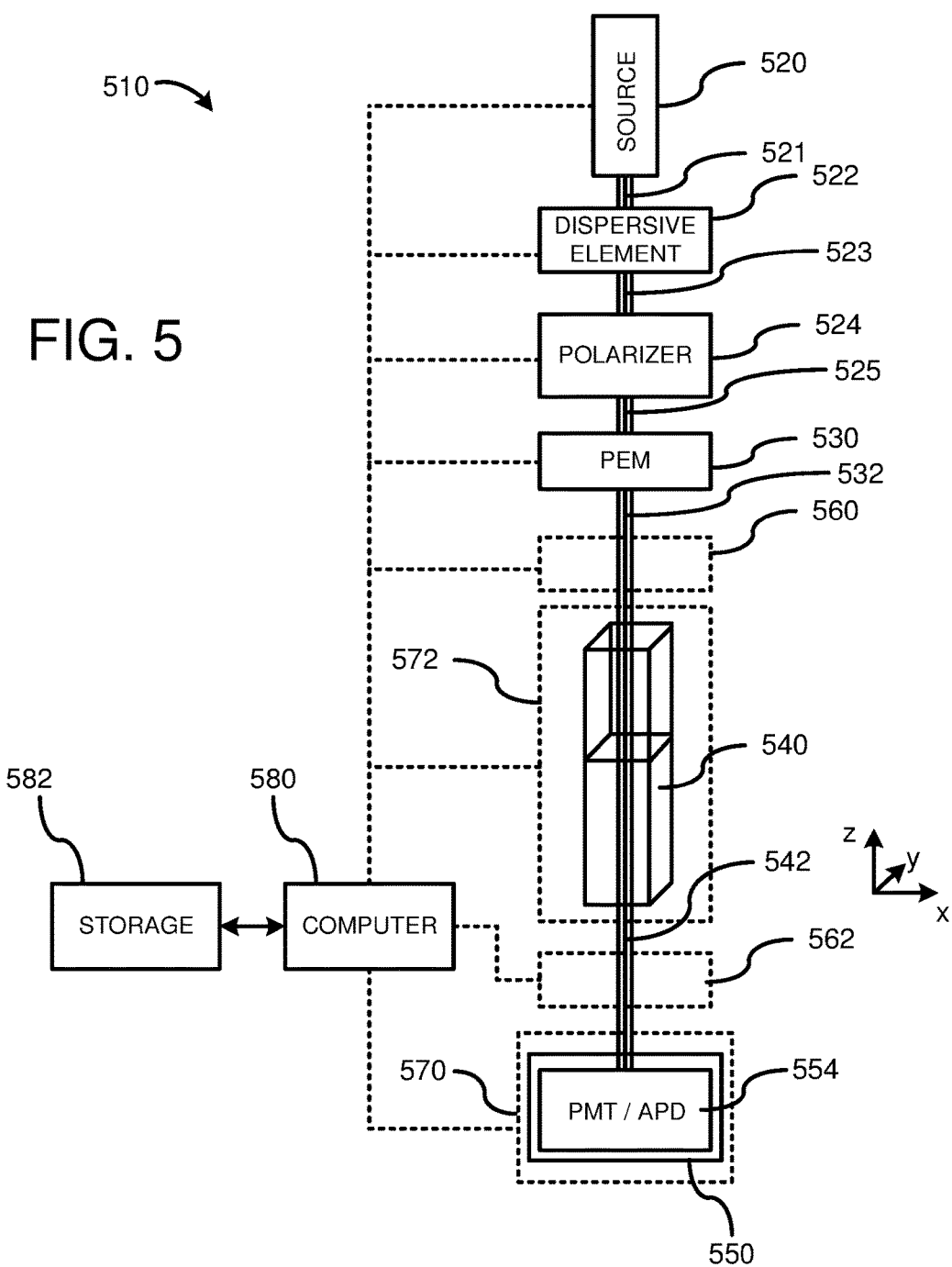
FIG. 5 is a block diagram of an embodiment of a CD spectrometer with a light source above the solution being measured in accord with an embodiment of the disclosed technology.

FIG. 5 depicts a block diagram of a first embodiment of a CD spectrometer system 510 in accordance with the disclosed technology. The system 510 generally includes a light source 520 configured to generate a light beam 521, a dispersive element 522, a polarizer 524, a photoelastic modulator or "PEM" 530, a contained sample 540, and a detection subsystem 550 (e.g., a subsystem that includes a photomultiplier tube or avalanche photodiode (APD)).

Also illustrated in FIG. 5 are one or more meniscus-effect-mitigating components or subsystems. For instance, in FIG. 5, a pre-sample optical lens 560 (which may be adjustable along any of the x, y, or z axes to adjust its focal point) is included in the system 510 before the light beam passes through the sample 540; a post-sample optical lens 562 (which may be adjustable along any of the x, y, or z axes to adjust its focal point) is included after the light beam passes through the sample; a z-axis translation system 570 is included that is configured to move the detection subsystem 550 toward or away from the bottom of the sample 540 along the z-axis; and/or a z-axis translation system 572 is included that is configured to move the sample 540 toward or away from the detection subsystem 550. Any one or more of these meniscus-effect-mitigating components or subsystems can be included in embodiments of the disclosed technology. For example, in particular embodiments, one or both of the optical lenses 560, 562 are included without any of the z-axis translational mechanisms 570, 572, while in other embodiments, one or more of the z-axis translational mechanisms 570, 572 are included without any of the lenses 560, 562. Still further, certain embodiments include combinations of any of the lenses 560, 562 together with the z-axis translational mechanisms 570, 572. Further, the lenses 560, 562 can themselves be respectively adjustable (manually or automatically) along the z-axis. The role and operation of these meniscus-effect-mitigating components and subsystems are discussed in more detail below.

In FIG. 5, the active components are controlled by computing hardware 580 (e.g., a processor or microcontroller), which can be further configured to perform the calculations for the sought-after polarimetric parameters. The measurements can be stored in a non-transitory storage device 582 (e.g., a hard-drive, solid-state memory device (such as Flash memory), RAM, or other such storage device mechanism) and/or displayed on a display device (e.g., via a user interface on a computer monitor or screen). The non-transitory storage device 582 can further store executable instructions for controlling the active components in the system. For instance, the non-transitory storage device 582 can store software for controlling one or more of the active meniscus-effect-mitigating components or subsystems in a manner that reduces the effect of the sample's meniscus on the measurements at detection subsystem 550.

In certain preferred embodiments, the system components are arranged so that the source light beam 521 travels through the sample 540 in a generally vertical direction, for reasons that will be explained more below. The light source 520 provides a relatively wide-bandwidth source light beam in the ultraviolet-visible-infrared ("UV-Vis-IR") spectral region (e.g., 180 nm to 1000 nm (UV-Vis-IR) or any subrange thereof). The source may be a single component or a combination of sources such as, a tungsten filament, a deuterium arc lamp, a laser-driven light source, a xenon arc lamp, or light emitting diodes (LED). Further, the light beam can have various diameters, but in certain implementations is 1 mm in diameter (e.g., +/−0.5 mm).

In the illustrated embodiment, the beam from the light source 520 is dispersed by a dispersive element 522. The dispersive element 522 may be, for example, a prism or diffraction grating. In operation, the source light beam 521 contains a wide range of wavelengths (before the dispersive element 522). The dispersive element 522 causes the source light beam 521 to be dispersed into many beams of different wavelengths, each of which has a different center wavelength and a different exit angle from the dispersive element. The dispersive element is typically contained in a housing comprising three main components: an entrance aperture, the dispersive element itself (e.g., the prism or diffraction grating), and an exit aperture. In particular implementations, the dispersive element can be rotated (or otherwise adjusted) to cause a different narrow band of beams to have an exit angle that passes through the exit aperture. In this way, the dispersive element 522 operates to selectively disperse and output narrow-banded beams of different wavelengths (e.g., beams having wavelengths of +/−0.5 nm around the center wavelength, full width of 1 nm at half height (FWHH) beams, or other such narrow-bandwidth beams). For example, and according to certain embodiments, the dispersive element 522 can be operated to sequentially output narrow-banded beams at a plurality of different wavelength bands such that only these beams having a narrower band of wavelengths are propagated through polarizer 524, PEM 530, pre-sample optical lens 560, sample 540, post-sample optical lens 562, and detection subsystem 550, thus allowing CD measurements to be obtained and computed for a given sample at a plurality of different narrow-band wavelengths. This operation is sometimes referred to as a "scanning" operation. The beam of narrower wavelengths output from the dispersive element 522 is sometimes referred to as the dispersed source light beam 523 (or dispersed beam).

Returning to FIG. 5, the dispersed source light beam 523 is directed through the polarizer 524 and into the aperture of the PEM 530. The PEM 530 modulates the dispersed source light beam 523 between right and left circular polarization at the modulator drive frequency (f) of, for example, 50 KHz, and produces a polarization modulated source light beam 525 (or polarization modulated beam). In this regard, an exemplary PEM 530 includes a quartz piezoelectric transducer that is bonded to an optical element through which the beam 525 passes. The leads of the transducer can be connected to a driver circuit under the control of the computer 580.

Although a PEM 530 is shown in FIG. 5 (and also in FIGS. 6, 14, and 31-33), other optical polarization modulation devices can be used in embodiments of the disclosed technology (e.g., in embodiments of the systems illustrated in FIGS. 5, 6, 14, and 31-33 in place of the PEM). For example, one or more rotating waveplates, liquid crystal modulators, or other such device configured to perform optical polarization modulation can be used in the system in place of (or in addition to) the PEM.

The polarization modulated source light beam 532 (sometimes referred to as the measuring beam or measuring light beam) is directed through the sample 540, which may be, for example, a contained chemical substance that exhibits CD. The light beam that emanates from the sample 540 (shown as emanating beam 542) carries the absorption information from the sample material.

The emanating beam 542 is then detected at the detection subsystem 550. In the illustrated embodiment, the detection subsystem 550 comprises a photomultiplier tube ("PMT") or avalanche photodiode ("APD"). For example, in certain embodiments, the PMT or APD is computer-controllable, has an appropriate spectral response, has a wide range of variable gains, and has a fast settling time when the gains are changed. Example PMTs include, for instance, Hamamatsu model H10426-01. Example APDs include Hinds APD model APD-100. In certain example embodiments, the spectral response max to min ratio is 100 or lower. Further, in certain implementations, the gain adjustment can be used to amplify the low response signals. The output of the photomultiplier tube can be passed through a phase sensitive detector (not shown), such as a lock-in amplifier. The phase sensitive detector can be correlated to the frequency of the PEM (e.g., 42 KHz, or other PEM frequency). Once the CD information is detected and computed (e.g., at a plurality of different narrow-band wavelengths), it can be stored in storage 582 and displayed to a user (e.g., via a user interface at a display device).

Figure 6:
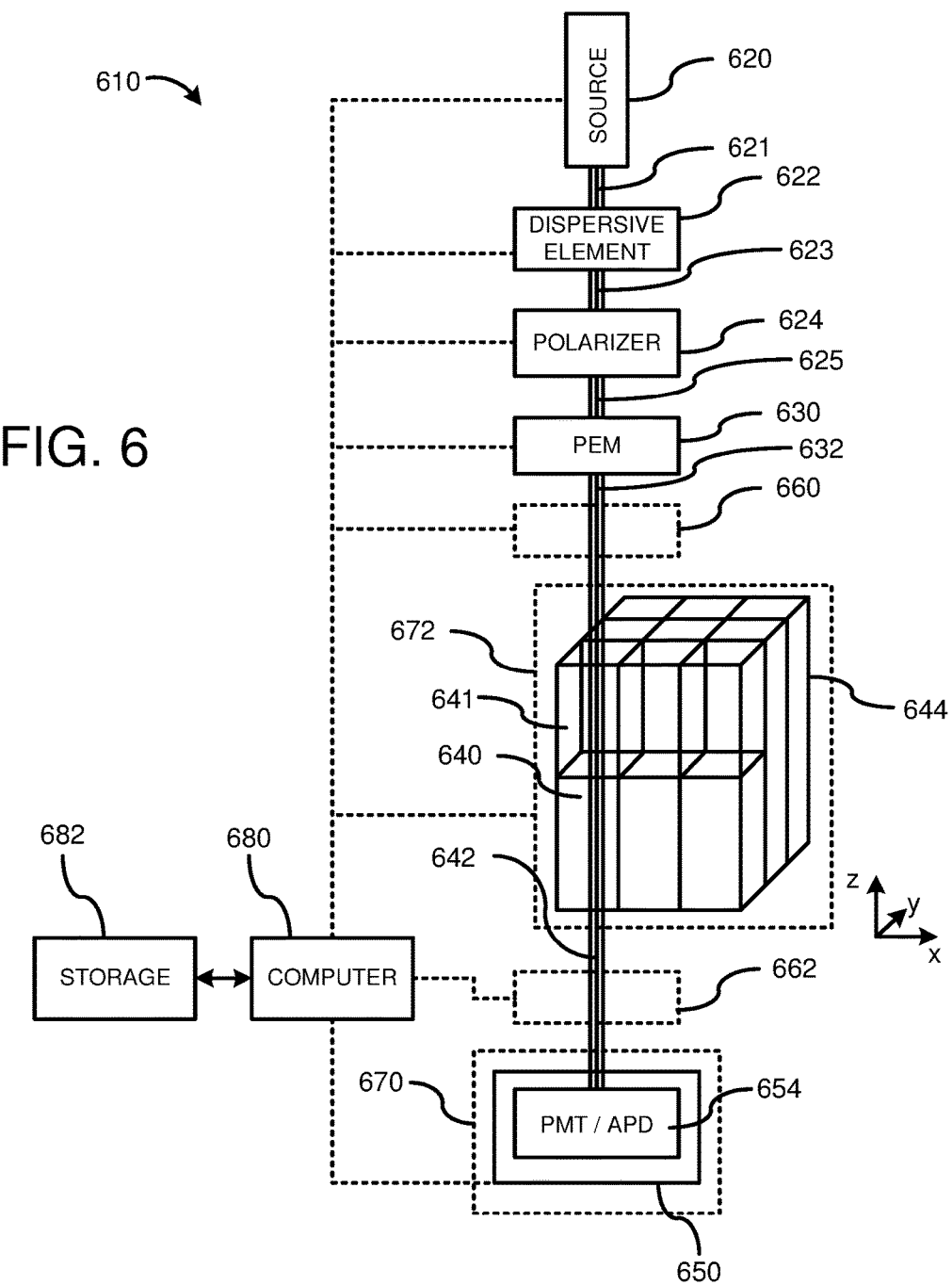
FIG. 6 is block diagram of an alternative embodiment of a CD spectrometer with a light source above the solution being measured in accord with the disclosed technology.

FIG. 6 is block diagram of an alternative embodiment of a CD spectrometer system 610 in accordance with the disclosed technology. The reference numerals in FIG. 5 have been increased by 100 for use in FIG. 6, and the components related by this numbering technique (light source 620 and PEM 630, for example) are to be considered the same unless described otherwise below.

In the embodiment of FIG. 6, the sample 640 is contained in one well 641 of a multi-well well plate 644. For simplicity, only nine wells in a 3×3 array are illustrated, with the understanding that the well plate 644 may comprise many more wells. The CD spectroscopy system 610 is typically configured to separately analyze the substances of each well, which most often contain different combinations of reagents as discussed above. The well plate 644 can have any of a variety of shapes, but in the embodiment discussed here is relatively flat and much shallower (as illustrated by the vertical z-direction of FIG. 6) than it is long and wide (as illustrated by the x- and y-directions of FIG. 6). Typically, the individual wells are sealed on all sides but for the top. The top may be covered in some cases when the well is filled. This well plate configuration lends itself well to use in a system 610 where the source beam 621 travels in a generally vertical direction.

In this embodiment, the overall speed of the system 610 is increased by an efficient way of analyzing the contents of each well of the well plate 644. In particular, by virtue of the vertically oriented beam, the source light beam 621 is transmitted directly through each one of the wells (e.g., well 641 and the other wells illustrated in FIG. 6) and CD measurements obtained (e.g., CD measurements at multiple narrow-band wavelengths for each respective solution in each well), rather than sequentially transporting the contents of each well into a separate sample cell of the system for analysis using a horizontally oriented beam. Consequently, the solution beam measured need not be removed from the well of the well plate, creating the potential for a significant increase in the speed with which measurements (e.g., CD measurements) can be obtained for solutions in a well plate.

For example, in particular embodiments, the well plate 644 is mounted in a controllable holder that can be operated (e.g., by the computer 680) to provide translational motion of the plate in the x and y directions as shown in FIG. 6, which define a plane that is perpendicular to the beam 621. The beam 621 is then directed through a selected well (and hence the sample solution contained within) between the four vertical walls that define each well of the well plate 644.

Any polarization effects that might be introduced to the light as it propagates through each well in 644 that contains only the solvents can be characterized and compensated for in the subsequent computation of CD values. In this regard, a well plate 644 containing only the solvents may be characterized in advance and have its corresponding polarization data stored as the baseline data. (e.g., by having the polarization data stored in an accessible database and/or by having machine readable code fixed to the plate).

The system 620 can also include a mechanism for removing a top cover of the well plate 644 prior to directing the beam 621 through the well, thereby obviating the need to characterize and compensate for the polarization effects of the cover. Alternatively, the cover could be characterized as part of the baseline data, as noted above.

It is also contemplated that an empty well plate could be placed in the holder and moved as discussed so that polarization parameters for each well could be collected and used to calibrate the system. The same well plate can then be used to analyze the contents of each well after the well plate is filled with samples.

There may be applications where it is undesirable to move the filled well plate 644. In such situations, the beam-line components of the system can be mounted into one or more movable systems that allow the components to be moved together such that the source beam 621 traverses the x-y plane to reach and propagate through each one of the wells (e.g., well 641) in the well plate 644. Alternatively, the source and detector modules could be substantially stationary but include associated beam re-direction components for redirecting the vertical path of only the source beam itself, rather than the entire module. In this alternative, however, polarization effects of any beam redirection components would desirably be accounted for in the CD computation.

As with the system 510 in FIG. 5, the system 610 also includes one or more meniscus-effect-mitigating components or subsystems. For instance, in FIG. 6, a pre-sample optical lens 660 (which may be adjustable along any of the x, y, or z axes to adjust its focal point) is included in the system 610 before the light beam passes through the sample 640; a post-sample optical lens 662 (which may be adjustable along any of the x, y, or z axes to adjust its focal point) is included after the light beam passes through the sample 640; a z-axis translation system 670 is included that is configured to move the detection subsystem 650 toward or away from the bottom of the well plate 644 along the z-axis; and/or a z-axis translation system 672 is included that is configured to move the well plate 644 toward or away from the detection subsystem 650. Any one or more of these meniscus-effect-mitigating components or subsystems can be included in embodiments of the disclosed technology. For example, in particular embodiments, one or both of the optical lenses 660, 662 are included without any the z-axis translational mechanisms 670, 672, while in other embodiments, one or more of the z-axis translational mechanisms 670, 672 are included without any of the lenses 660, 662. Still further, certain embodiments include combinations of any of the lenses 660, 662 together with the z-axis translational mechanisms 670, 672. The role and operation of these meniscus-effect-mitigating components and subsystems are discussed in more detail below.

In the embodiments illustrated in FIGS. 5 and 6, a PMT or APD is used in the detection subsystems 550, 650, respectively. In other embodiments, however, a charge-coupled device (CCD) is used in the detection subsystem. Example embodiments of such systems are shown as systems 3110 and 3210 in FIGS. 31 and 32, which are discussed in more detail below.

Figure 31:
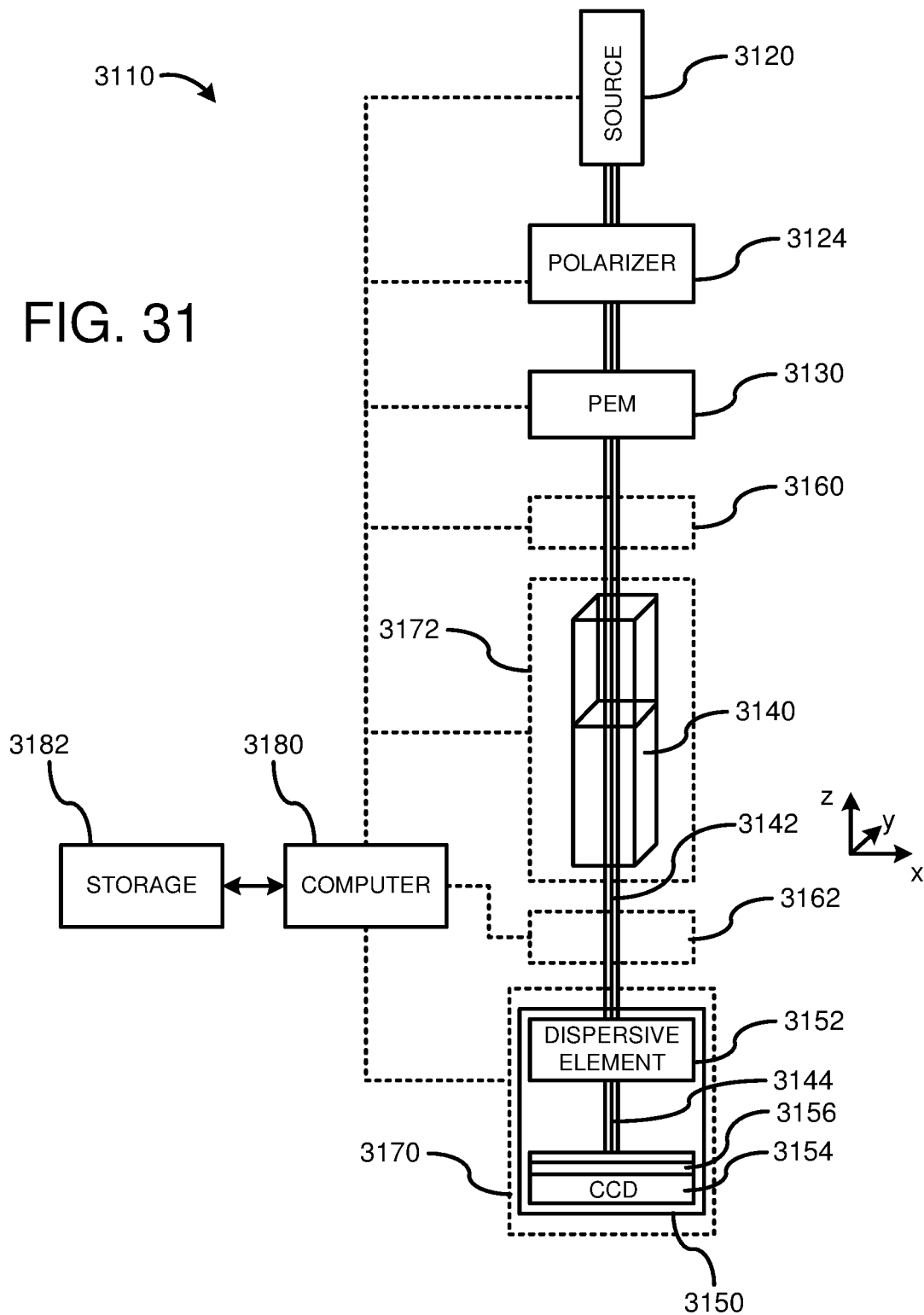
FIGS. 31-33 are block diagrams of further embodiments of example CD spectrometers in accordance with the disclosed technology.
Figure 32:
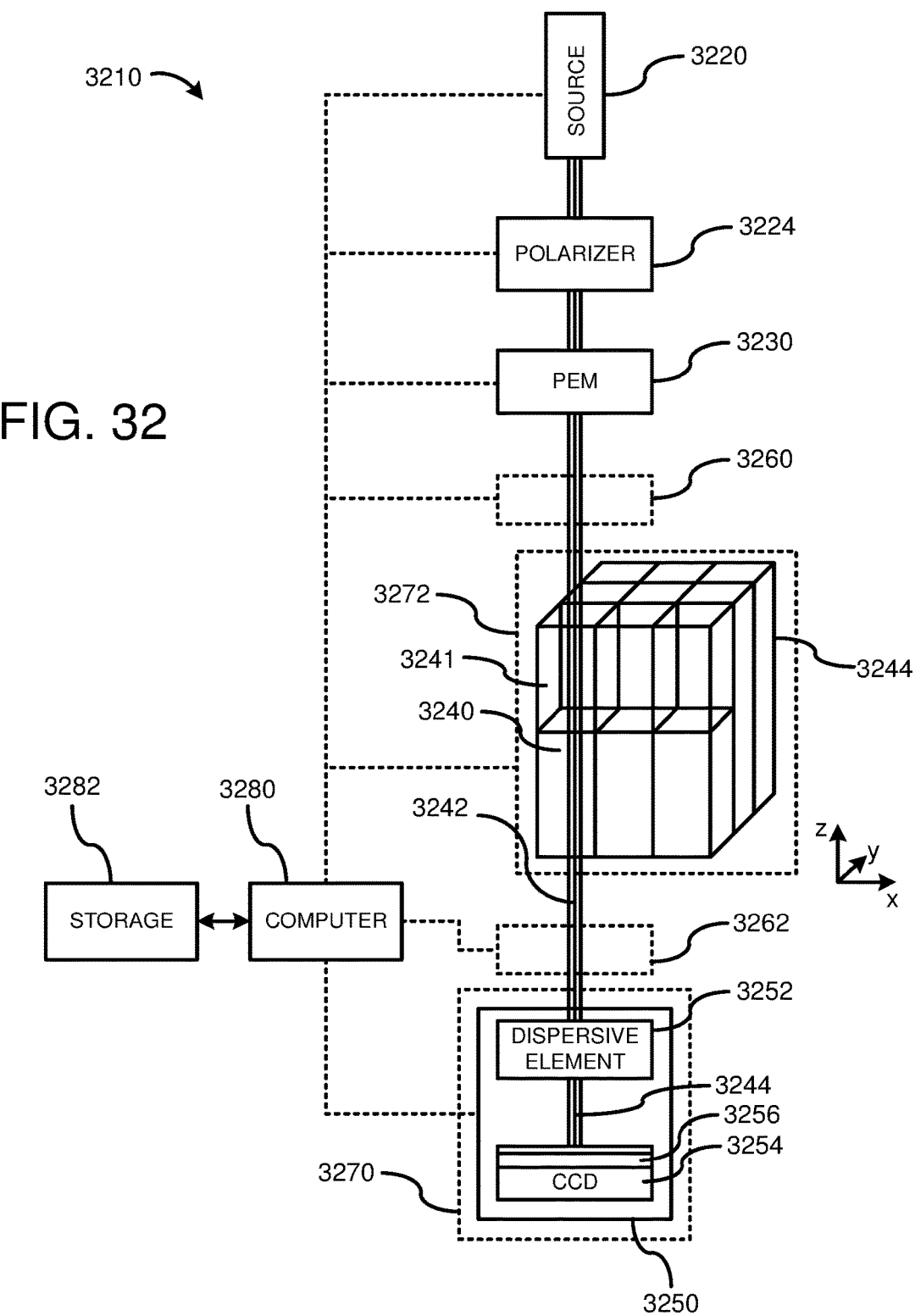

In FIGS. 31 and 32, most of the elements of FIGS. 5 and 6 are still present and have reference numerals that have been increased to the 3100s and 3200s, respectively. The components related by this numbering technique (light source 3120 and PEM 3130, for example) are to be considered the same unless described otherwise below. In contrast to FIGS. 5 and 6, the detection subsystems 3150, 3250 in FIGS. 31 and 32 include a charge-coupled device 3154, 3254 and the dispersive element (renumbered as 3152, 3252) is relocated to be part of the detection subsystem 3150, 3250 and placed in front of an active region of the CCD 3154, 3254.

In these embodiments, the source light beam that is directed through the sample has a relatively wide bandwidth in the UV-Vis-IR spectral region. The wide-bandwidth light beam that emanates from the sample 3140, 3240 (shown as emanating beam 3142, 3242) carries the absorption information from the sample material. In the illustrated implementations, the emanating beam 3142, 3242 is dispersed by dispersive element 3152, 3252 of the detection subsystem 550 into a plurality of relatively narrower bandwidth "separate" beams 3144, 3244 for simultaneous spectroscopic detection. The dispersive element 3152, 3252 may be, for example, a prism or diffraction grating.

Each of the several separate beams 3144, 3244 (which, as noted, comprises a narrow band of wavelength and, thus, only a portion of the entire UV-Vis-IR bandwidth of the emanating beam 3142, 3242) is individually detected simultaneously with each one of the other separate beams 3144, 3244. To this end, the detection subsystem 3150, 3250 in certain example embodiments comprises a fast gated, intensified CCD (or ICCD). The CCD thus includes a gain mask 3156, 3256 that is controlled by the computer 3180, 3280 or dedicated controller operated by the computer.

In general, the CCD response frequency is significantly lower than the drive frequency of the PEM 3130, 3230. Consequently, the gain mask 3156, 3256 is controlled to be driven in synchrony with the drive frequency of the PEM 3130, 3230 so that the mask is open for a short time, for example, corresponding to one-quarter of the PEM modulation period or T=(1/f), and then turned off during the remaining three-quarters of the PEM modulation period. The light information that periodically reaches the detector is later processed (integrated) to adjust for the effects of the intermittent gating.

The signal corresponding to the each of the gated, separate beams 3144, 3244 is acquired via a dedicated channel of the detection subsystem 3150, 3250. The CCD of the example detection subsystem 3150, 3250 can include, for example, a CCD such as one manufactured by Andor Technology, of Belfast, Northern Ireland, and marketed under the trade name "iStar ICCD Camera." The camera pixel format may be generally elongated (for example, 1600×200 pixels) to include a number (e.g., 1600) of discrete spectral channels, with each channel associated with a number (e.g., 200) of related averaging or "binning" columns of pixels. Each separate beam 3144, 3244 is directed to a corresponding spectral channel, with subsequent ones of the gated beams 3144, 3244 binned in the columns for averaging and readout to the computer 3180, 3280. It will be appreciated that this essentially simultaneous detection of the dispersed, separate beams 3144, 3244 will greatly increase the speed with which the CD parameter can be calculated, as compared to the sequential detection techniques of other approaches. Once the CD information is computed, it can be stored in storage 3182, 3282 and displayed to a user.

As an alternative to gating in time the separate beams 3144, 3244, the disclosed technology contemplates gating or flashing the light source 3120, 3220 at a fraction of the PEM modulation frequency. To this end, a controller associated with the light source 3120, 3220 can be used that is in communication with the computer 3180, 3280 to be driven in synchrony with the PEM modulation so that the source light beam 3120, 3220 is turned on and off (flashed) in fractions of the PEM drive frequency. Thus, the relatively slower detector CCD 3154, 3254, which need not be gated in this embodiment, will correctly receive the separate beam information in discrete time intervals.

As with the systems of FIGS. 5 and 6, systems 3110 of FIG. 31 and 3210 of FIG. 32 include one or more meniscus-effect-mitigating components or subsystems. For instance, the systems 3110, 3210 can include any of: one or more of pre-sample optical lenses 3160, 3260 (which may be adjustable along any of the x, y, or z axes to adjust its focal point); one or more post-sample optical lenses 3162, 3262 (which may be adjustable along any of the x, y, or z axes to adjust its focal point); a z-axis translation system 3170, 3270 to move the detection subsystem toward or away from the bottom of the well plate along the z-axis; and/or a z-axis translation system 3172, 3272 to move the well plate toward or away from the detection subsystem. Any one or more of these meniscus-effect-mitigating components or subsystems can be included in embodiments of the disclosed technology.

C. Mitigating Meniscus Effects

As explained above with respect to FIGS. 5, 6, 31, and 32, one or more meniscus-effect-mitigating components or subsystems can be included in a spectroscopy system (e.g., in a CD spectrometer using a vertical beam orientation) to help reduce and/or compensate for the effects of the meniscus at the top surface of a sample being measured. Example embodiments of these components and/or subsystems are discussed in the subsections below. Any one or more of these meniscus-effect-mitigating components or subsystems can be included in embodiments of the disclosed technology.

In FIGS. 7-13 and 15-21, certain portions of the spectroscopy system are not shown for ease of illustration (e.g., the beam source, polarizer, and PEM) but are understood to be present in embodiments of the disclosed technology. Further, the detection subsystem is shown as a single block for ease of illustration but is to be understood to potentially contain several components as explained above (e.g., a photomultiplier tube (PMT), avalanche photodiode (APD), or a CCD and, optionally, a dispersive element). The active detection surface of the detection subsystem, then, is the active detection surface of the PMT, APD, or CCD (when it comprises the first element in the detection subsystem, or the operational surface of the dispersive element when it comprises the first element in the detection subsystem). Further, the examples described below in FIGS. 7-13 and 15-21 also concern CD spectroscopy of a well in a well plate. It is to be understood that the techniques can be adapted for other systems as well, such as those with a single sample holder (as in FIG. 4) or any spectroscopy system in which meniscus affects are desirably reduced.

1. Mechanical Methods to Increase the Active Area of the Detector

Figure 7A:
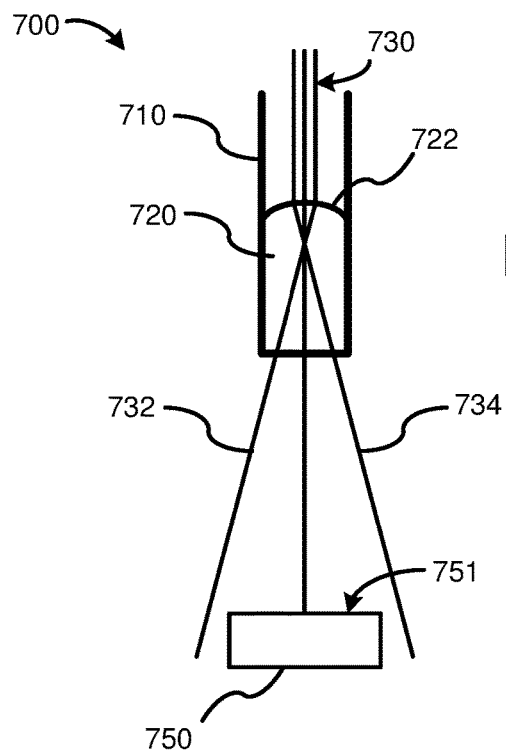
FIGS. 7A-7C are block diagrams illustrating mechanical techniques for reducing meniscus effects in systems having a light source located above the solution being measured.
Figure 7B:
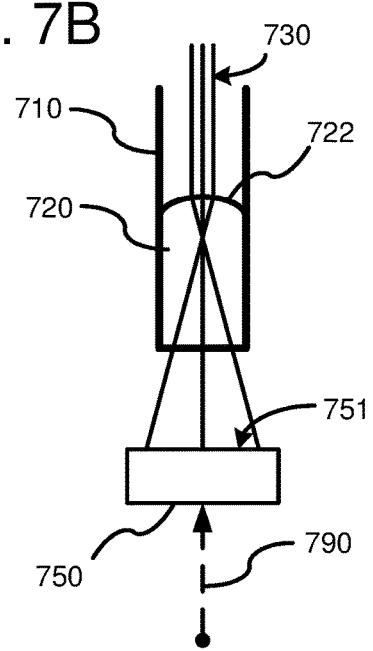
Figure 7C:
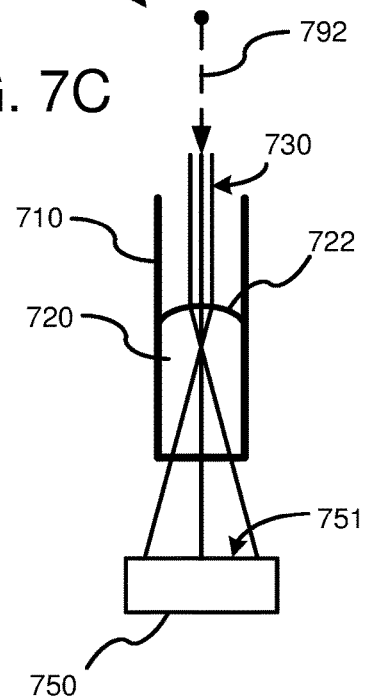

In some embodiments, the distance between the detection subsystem and the well plate is adjustable. Thus, in certain implementation, the distance can be shortened (e.g., to a practical minimum or to any point in which sufficient signal contacts the detecting surface of the detection subsystem to produce a desired signal-to-noise ratio at the detection subsystem). FIGS. 7A-7C are cross-sectional side views illustrating the effect of such adjustments. FIG. 7A is a cross-sectional side view illustrating the case where the beam divergence caused by a meniscus 722 prevents at least a portion of the beam from being incident on the active detecting surface 751 of the detection subsystem 750. More specifically, FIG. 7A is a block diagram 700 showing a cross-sectional side view of a well 710 in a well plate containing a solution 720 and having a vertically oriented beam 730 incident on a top surface of the solution 720. In FIG. 7A the beam originates from above the well 710 (e.g., as part of a CD spectroscopy system as explained above). Further, the top surface of the solution 720 forms a convex meniscus 722, which acts as a convergent lens for the incident beam 730. In FIG. 7A, the curvature of the meniscus 722 is large enough such that the incident beam has an angle of refraction that causes the focal point to be within the solution 720 and to then diverge in such a manner that portions of the beam are not incident on an active detection area 751 of the detection subsystem 750 (as illustrated by beam edges 732, 734). Consequently, the signal detected at the detection subsystem 750 will be diminished and the signal-to-noise ratio reduced.

FIG. 7B is similar to FIG. 7A, but shows that the detection subsystem 750 can be moved (e.g., translated along the z axis) upward toward the bottom of the well 710. This upward translation is illustrated by arrow 790. By doing so, the same active detection area 751 on the detection subsystem 750 will receive a higher percentage of the light beam 730 interrogating the solution (and potentially all of the light beam 730 as illustrated). Consequently, the signal detected at the detection subsystem 750 can be improved and the signal-to-noise ratio increased (e.g., to its maximum possible value when adjusted to receive the entirety of the beam). The adjustable positioning of the detection subsystem 750 can be provided through a manually adjusted mechanism (e.g., screws or pegs along a z-axis track on which the detection subsystem 750 is mounted) or using a computer-controlled adjustment mechanism (e.g., servo-controlled or other motorized mechanism). For example, the detection subsystem 750 can be mounted on a computer-controlled translational stage that can be automatically controlled to adjust the distance between the detector and the well plate. Further, because the solution may vary for different analyses, or for each well, the curvature of the top surface (the curvature of the meniscus) may vary and consequently its index of refraction. Accordingly, the computer-controlled mechanism can be used to provide individual adjustments for each individual well of the well plate as needed.

FIG. 7C shows a further approach to adjusting the location of the detection subsystem 750 relative to the bottom of the well 710. In FIG. 7C, the well plate including the well 710 is moved downward toward the detection subsystem 750. This downward translation is illustrated by arrow 792. As in FIG. 7B, the position adjustment causes the active detection area 751 of the detection subsystem 750 to receive a higher percentage of the light beam 730 interrogating the solution (and potentially all of the light beam 730, as illustrated), thus increasing the signal-to-noise ratio (e.g., potentially to its maximum possible value when adjusted to receive the entirety of the beam). The adjustable positioning of the well plate (and thus the well 710) can be provided through a manually adjusted mechanism (e.g., screws or pegs along a z-axis track on which the well plate is mounted) or using a computer-controlled automatic adjustment mechanism (e.g., a servo-controlled or other motorized mechanism). Further, the adjustment mechanism can be attached to other portions of the system as well (e.g., the light source, polarizer, PEM, any pre-solution optical components, and/or or other pre-solution components).

Embodiments of the disclosed technology also include systems that have both an adjustable detection subsystem (as in FIG. 7B) and an adjustable well plate (as in FIG. 7C).

Further, the shortest distance between the detector and the well plate is not always the optimized condition. For example, for certain systems, it may be desirable to have the maximum amount of the active detection surface interfacing with the beam (as opposed to having the beam tightly focused on the detection surface), in which case the distance would likely be larger than the shortest distance.

Additionally, in certain situations (such as those illustrated in FIG. 4), it would be advantageous to include apertures at the entrance point of the detection subsystem. In such cases, the apertures can have varying diameters and can be either manually or computer-controlled. The apertures can be used to "clean" the beam that is passed through to the detection components to avoid measurement artifacts. For example, an adjustable aperture could be used to block any portion of the beam resulting from the internal reflects caused by the vertical walls of the well (as illustrated by dashed lines 436, 438 in FIG. 4) from passing to the detection components (e.g., the PMT, APD, or CCD) of the detection subsystem.

In other embodiments, the size of the active detection area of the detection subsystem can be adjusted. For example, in order to mitigate meniscus effects, the system can be modified to use a detection subsystem having a larger active detection area. This approach is useful in situations where the distance between the sample and the detection subsystem is fixed and cannot be modified.

2. Optical Techniques

In some embodiments, one or more lenses are used to reduce the effect of a solution's surface meniscus on the resulting measurement made by the detection subsystem. As more fully explained below, one or more lenses can be located prior to the beam passing through the solution (referred to as "pre-solution" lenses) or after the beam passing through the solution (referred to as "post-solution" lenses).

Figure 8:
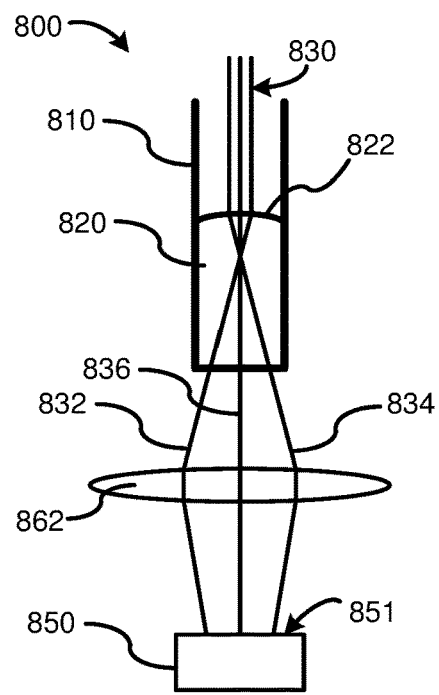
FIGS. 8-13 are block diagrams illustrating optical components for reducing meniscus effects in systems having a light source located above the solution being measured.
Figure 9:
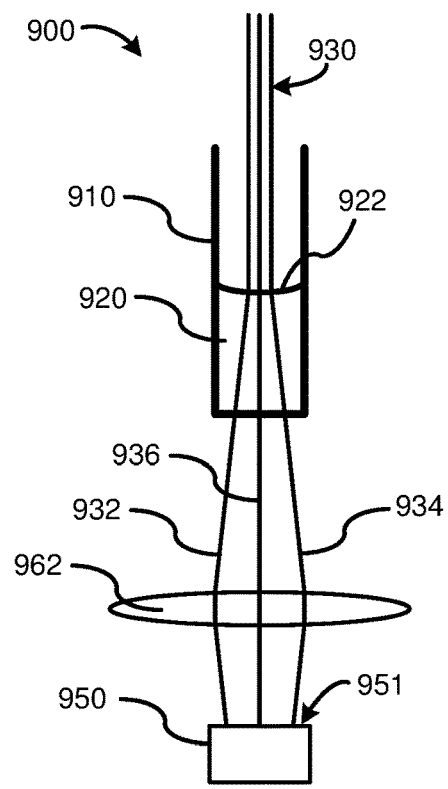

FIGS. 8 and 9 illustrate examples in which one or more lenses (illustrated as a single lens but which may actually comprise a plurality of lenses) are positioned in a location after the beam passes through the well of a well plate (e.g., as post-solution components).

In particular, FIG. 8 is a block diagram 800 showing a cross-sectional side view of a well 810 containing a solution 820 and having a vertically oriented beam 830 incident on a top surface of the solution 820. In FIG. 8 the beam originates from above the well 810 (e.g., as part of a CD spectroscopy system as explained above). Further, the top surface of the solution 820 forms a convex meniscus 822, which acts as a convergent lens for the incident beam 830. In FIG. 8, the curvature of the meniscus 822 is large enough such that the incident beam 830 refracts to create an unintended focal point (either in the solution 820 or out of the solution) and to subsequently have beam edges 832, 834 that diverge from a beam center point 836. A lens 862 is positioned between the bottom of the well 810 (and thus the well plate) and the detection subsystem 850. The illustrated lens 862 is a convergent lens (e.g., any suitable convergent lens) that causes the beam to converge (or at least reduces the degree of divergence in the beam). Further, the lens 862 is located in a position (e.g., a position along the z-axis) that re-focuses the beam such that a greater percentage of the beam is incident upon an active detecting surface 851 of the detection subsystem 850 than in the case without the lens 862. Accordingly, the signal at the detection subsystem 850 can be improved and the signal-to-noise ratio increased. Further, in particular embodiments, the lens 862 can be adjustable along the z-axis to change its focal point. For instance, the lens 862 can be adjustable through a manually adjusted mechanism (e.g., screws or pegs along a z-axis track on which the detection subsystem 850 is mounted) or using a computer-controlled automatic adjustment mechanism (e.g., a servo-controlled or other motorized mechanism). Further, in certain embodiments, the power of the lens itself is adjustable (e.g., by switching to a different lens with a different power (focal length)).

FIG. 9 is similar to FIG. 8 but shows the situation in which a solution 920 in a well 910 forms a concave meniscus 922, which acts as a divergent lens for the incident beam 930. In FIG. 9, a lens 962 is positioned between the bottom of the well plate and the detection subsystem 950. The illustrated lens 962 is a convergent lens (e.g., any suitable convergent lens) that causes the beam to converge (or at least reduces the degree of divergence in the beam). Further, the lens 962 is located in a position (e.g., a position along the z-axis) that re-focuses the beam such that a greater percentage of the beam is incident upon an active detecting surface 951 of the detection subsystem 950 than in the case without the lens 962. Accordingly, the signal at the detection subsystem 950 can be improved and the signal-to-noise ratio increased. Further, and as explained above with respect to FIG. 8, the lens 962 can be adjustable along the z-axis to change its focal point.

Figure 10:
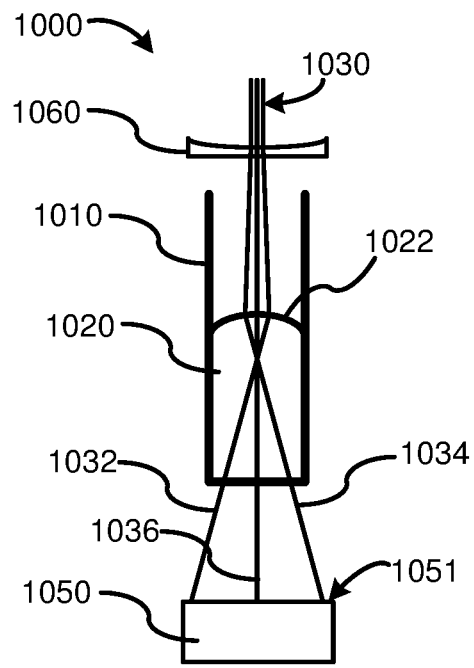
Figure 11:
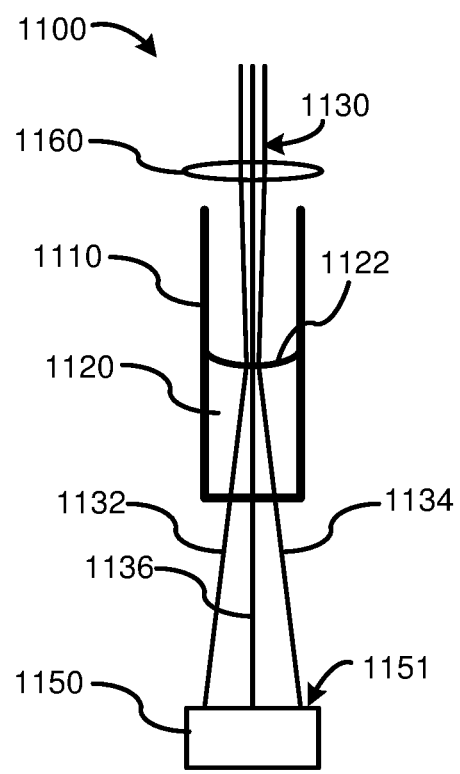

FIGS. 10 and 11 illustrate examples in which one or more lenses (illustrated as a single lens but which may actually comprise a plurality of lenses) are positioned in a location before the beam passes through the well of a well plate (e.g., as pre-solution components).

In particular, FIG. 10 is a block diagram 1000 showing a cross-sectional side view of a well 1010 containing a solution 1020 and having a vertically oriented beam 1030 incident on a top surface of the solution 1020. In FIG. 10 the beam originates from above the well 1010 (e.g., as part of a CD spectroscopy system as explained above). Further, the top surface of the solution 1020 forms a convex meniscus 1022, which acts as a convergent lens for the incident beam 1030. In FIG. 10, the curvature of the meniscus 1022 is large enough such that the incident beam 1030 refracts to create an unintended focal point (either in the solution 1020 or out of the solution) and to subsequently have beam edges 1032, 1034 that diverge from a beam center point 1036. Further, in some cases, the divergence effect caused by the meniscus 1022 can be so great that the beam edges 1032, 1034 interact with the vertical walls of the well 1010 itself in the absence of any lens, as shown in FIG. 1. This situation can significantly affect the quality and usefulness of the resulting measurements. In FIG. 10, a lens 1060 is positioned above the top of the well 1010 (e.g., between the top of the well plate and a PEM (not shown). The illustrated lens 1060 is a divergent lens (e.g., any suitable divergent lens) that causes the beam to diverge. Further, the lens 1060 is located in a position (e.g., a position along the z-axis) that causes the summation of the divergent effect of the lens 1060 and the convergent effect of the meniscus 1022 to result in a greater percentage of the beam being incident upon an active detecting surface 1051 of the detection subsystem 1050 than in the case without the lens 1060. Accordingly, the signal at the detection subsystem 1050 can be improved and the signal-to-noise ratio increased. Further, in particular embodiments, the lens 1060 can be adjustable along the z-axis. For instance, the lens 1060 can be adjustable through a manually adjusted mechanism (e.g., screws or pegs along a z-axis track on which the detection subsystem 850 is mounted) or using a computer-controlled automatic adjustment mechanism (e.g., a servo-controlled or other motorized mechanism). Further, in certain embodiments, the power of the lens itself is adjustable (e.g., by switching to a different lens with a different power (focal length)).

FIG. 11 is similar to FIG. 10 but shows the situation in which a solution 1120 in a well 1110 forms a concave meniscus 1122, which acts as a divergent lens for the incident beam 1130. In FIG. 11, a lens 1160 is positioned above the top of the well 1110 (e.g., between the top of the well plate and a PEM (not shown). The illustrated lens 1160 is a convergent lens (e.g., any suitable convergent lens) that causes the beam to converge (or at least reduces the degree of divergence in the beam). Further, the lens 1160 is positioned above the top of the well 1110 (e.g., between the top of the well plate and a PEM (not shown)). The lens 1160 is located in a position (e.g., a position along the z-axis) that causes the summation of the convergent effect of the lens 1160 and the divergent effect of the meniscus 1122 to result in a greater percentage of the beam being incident upon an active detecting surface 1151 of the detection subsystem 1150 than in the case without the lens 1160. Accordingly, the signal at the detection subsystem 1150 can be improved and the signal-to-noise ratio increased. Further, in particular embodiments and as explained above with respect to FIG. 10, the lens 1160 can be adjustable along the z-axis.

Figure 12:
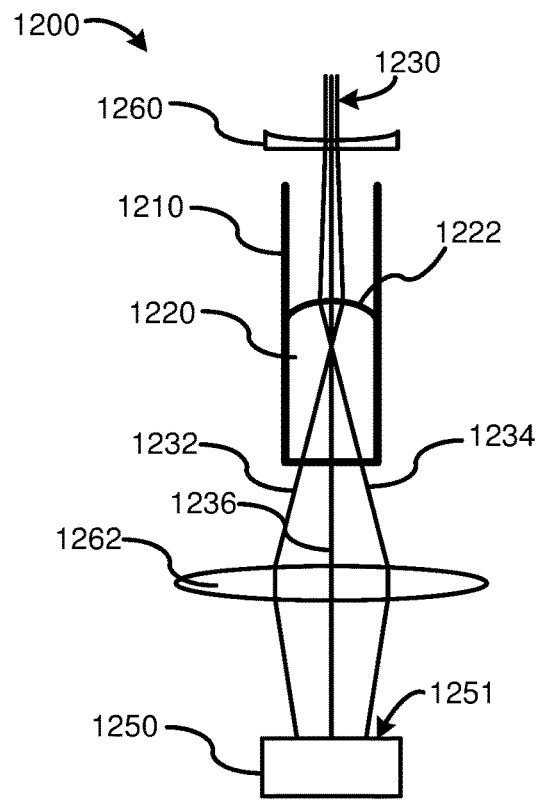
Figure 13:
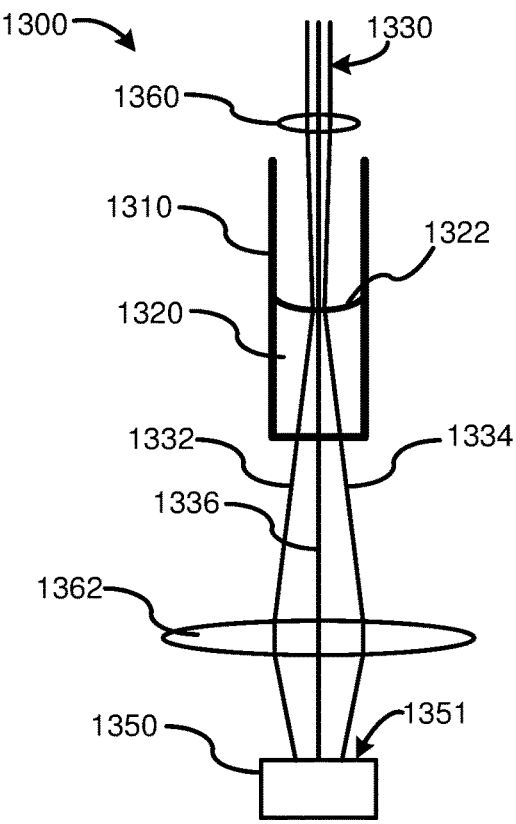

FIGS. 12 and 13 illustrate examples in which a first set of one or more lenses (illustrated as a single lens but which may actually comprise a plurality of lenses) are positioned in a location before the beam passes through the well of a well plate, and a second set of one or more lenses (illustrated as a single lens but which may actually comprise a plurality of lenses) are positioned in a location after the beam passes through the well of a well plate.

In particular, FIG. 12 is a block diagram 1200 showing a cross-sectional side view of a well 1210 containing a solution 1220 and having a vertically oriented beam 1230 incident on a top surface of the solution 1220. In FIG. 12 the beam originates from above the well 1210 (e.g., as part of a CD spectroscopy system as explained above). Further, the top surface of the solution 1220 forms a convex meniscus 1222, which acts as a convergent lens for the incident beam 1230. In FIG. 12, the curvature of the meniscus 1222 is large enough such that the incident beam 1230 refracts to create an unintended focal point (either in the solution 1220 or out of the solution) and to subsequently have beam edges 1232, 1234 that diverge from a beam center point 1236. A first pre-solution lens 1260 is positioned above the top of the well 1210 (e.g., between the top of the well plate and a PEM (not shown)). The illustrated pre-solution lens 1260 is a divergent lens (e.g., any suitable divergent lens) that causes the beam to diverge. A second post-solution lens 1262 is positioned below the bottom of the well 1210 (e.g., between the bottom of the well plate and an active detecting surface 1251 of detection subsystem 1250). The illustrated post-solution lens 1260 is a convergent lens (e.g., any suitable convergent lens) that causes the beam to converge. Further, the pre-solution lens 1260 and the post-solution lens 1262 are located in positions (e.g., respective positions along the z-axis) that cause the summation of the divergent effect of the pre-solution lens 1260, the convergent effect of the meniscus 1222, and the convergent effect of the post-solution lens 1262 to result in a greater percentage of the beam being incident upon an active detecting surface 1251 of the detection subsystem 1250 than in the case without the lenses 1260, 1262. Accordingly, the signal at the detection subsystem 1250 can be improved and the signal-to-noise ratio increased. Further, in particular embodiments, either one or both of the lenses 1260, 1262 can be adjustable along the z-axis. For instance, either one or both of the lenses 1260, 1262 can be adjustable through a manually adjusted mechanism (e.g., screws or pegs along a z-axis track on which the detection subsystem is mounted) or using a computer-controlled automatic adjustment mechanism (e.g., a servo-controlled or other motorized mechanism).

FIG. 13 is similar to FIG. 12 but shows the situation in which a solution 1320 in a well 1310 forms a concave meniscus 1322, which acts as a divergent lens for the incident beam 1330. In FIG. 13, a first pre-solution lens 1360 is positioned before the beam passes through the solution (as above in FIG. 12) and a second post-solution lens 1362 is positioned after the beam passes through the solution (as above in FIG. 12.) The illustrated pre-solution lens 1360 is a convergent lens (e.g., any suitable convergent lens) that causes the beam to converge, and the post-solution lens 1362 is a convergent lens (e.g., any suitable convergent lens). Further, the lenses 1360, 1362 are located in respective positions (e.g., a positions along the z-axis) that cause the summation of the convergent effect of the lens 1360, the divergent effect of the meniscus 1322, and the convergent effect of the lens 1362 to result in a greater percentage of the beam being incident upon an active detecting surface 1351 of the detection subsystem 1350 than in the case without the lenses 1360, 1362. Accordingly, the signal at the detection subsystem 1350 can be improved and the signal-to-noise ratio increased. Further, in particular embodiments and as explained above with respect to FIG. 12, one or more both of the lenses 1360, 1362 can be adjustable along the z-axis.

D. Alternative Beam Source Locations

In the embodiments described above, the beam source was located above the sample. However, the disclosed technology also include embodiments in which the beam source is located below the sample (e.g., below the bottom of a well plate). In FIGS. 15-21, the beam source is located below the sample. Any one or more of the advantages experienced in the embodiments in FIGS. 7-13 above can be enjoyed in the embodiments in FIGS. 15-21 in which the beam source is located below the sample. Further, in some cases, the embodiments in FIGS. 15-21 may be desirable. For instance, if the wells of the well plate are filled above their halfway point (e.g., to 0.75 of their capacity or to near or at their filling point), the embodiments discussed below may be desirable because the possibility of the beam being refracted by the meniscus of the solution and interacting with the vertical side walls of a well is reduced when a beam source below the well is used.

Figure 14:
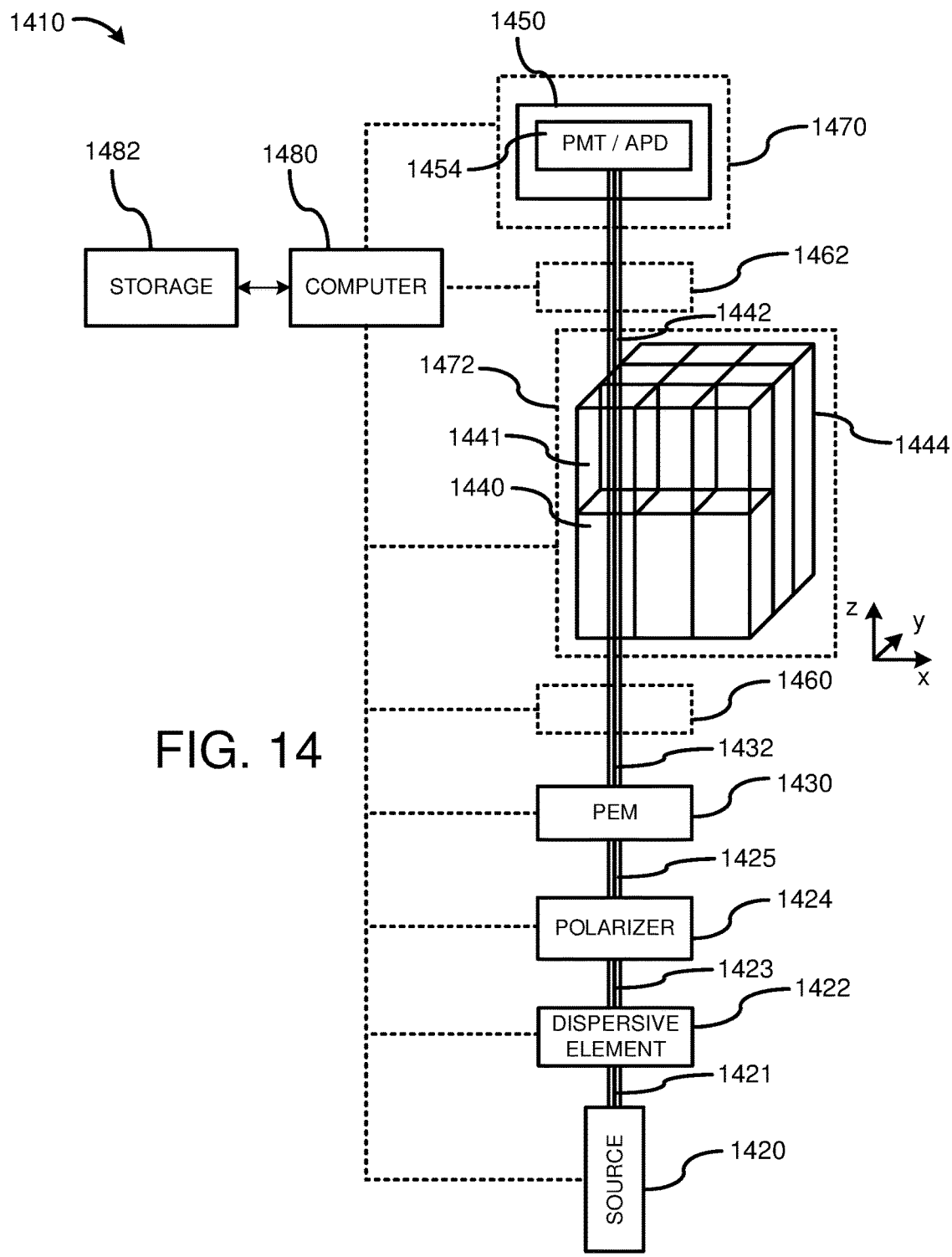
FIG. 14 is a block diagram of an embodiment of a CD spectrometer with a light source below the solution being measured in accord with an embodiment of the disclosed technology.

FIG. 14 is similar to FIGS. 5 and 6 above but illustrates an embodiment of a system 1410 for performing CD spectroscopy of respective solutions in wells of a well plate using a beam source located below the sample. In more detail, FIG. 14 depicts a block diagram of a third embodiment of a CD spectrometer system 1410 in accordance with the disclosed technology. The reference numerals in FIG. 14 have been increased to the 1400s for use in FIG. 14, and the components related by this numbering technique (light source 1420 and PEM 1430, for example) are to be considered the same as in FIG. 5 or 6 unless described otherwise below. As with systems 510 and 610, the system 1410 generally includes a light source 1420 configured to generate a light beam, a dispersive element 1422, a polarizer 1424, a photoelastic modulator or "PEM" 1430, a contained sample 1440, and a detection subsystem 1450 (e.g., a subsystem that includes a photomultiplier tube (PMT) or avalanche photodiode (APD)).

In FIG. 14, the light source 1420, dispersive element 1422, polarizer 1424, and PEM 1430 are located below the sample 1440 located in a well of a well plate as in FIG. 6, though the sample can be a single sample as in FIG. 5.

Also illustrated in FIG. 14 are one or more meniscus-effect-mitigating components or subsystems. For instance, in FIG. 14, a pre-sample optical lens 1460 is included in the system 1410 before the light beam passes through the sample 1440; a post-sample optical lens 1462 is included after the light beam passes through the sample; a z-axis translation system 1470 is included that is configured to move the detection subsystem 1450 toward or away from the top of the sample 1440 along the z-axis; and/or a z-axis translation system 1472 is included that is configured to move the sample 1440 toward or away from the detection subsystem 1450. Any one or more of these meniscus-effect-mitigating components or subsystems can be included in embodiments of the disclosed technology. For example, in particular embodiments, one or both of the optical lenses 1460, 1462 without any of the z-axis translational mechanisms 1470, 1472, while in other embodiments, one or more of the z-axis translational mechanisms 1470, 1472 are included without any of the lenses 1460, 1462. Still further, certain embodiments include combinations of any of the lenses 1460, 1462 together with the z-axis translational mechanisms 1470, 1472. Further, the lenses 1460, 1462 can themselves be respectively adjustable (manually or automatically) along the z-axis. The role and operation of these meniscus-effect-mitigating components and subsystems are substantially similar to the embodiments described above with respect to FIGS. 5-13 and are summarized below.

In FIG. 14, the active components can be controlled by computing hardware 1480 (e.g., a processor or microcontroller), which can be further configured to perform the calculations for the sought-after polarimetric parameter. The measurements can be stored in a non-transitory storage device 1482 and/or displayed on a display device as above with respect to FIGS. 5 and 6. The non-transitory storage device 1482 can further store executable instructions for controlling the active components in the system.

As in FIG. 6, the sample 1440 of FIG. 14 is contained in one well 1441 of a multi-well well plate 1444 (sometimes referred to as a microplate). For simplicity, only nine wells in a 3×3 array are illustrated, with the understanding that the microplate 1444 may comprise many more wells, each of which may be filled with a separate (and potentially distinct) sample. The CD spectroscopy system 1410 is typically configured to separately analyze the substances of each well, which most often contain different combinations of reagents as discussed above. The well plate 1444 can have any of a variety of shapes.

In the illustrated embodiment, the overall speed of the system 1410 is enhanced by the source light beam being sequentially directed vertically through each well of the well plate 1444. As one aspect of this approach, the source light beam 1421 (after being modified by the dispersive element 1422, polarizer 1424, and PEM 1430 to create a polarization modulated source light beam 1432) is directed through each one of the wells (e.g., well 1441 and the other wells illustrated in FIG. 14) and CD measurements obtained (e.g., CD measurements at multiple narrow-band wavelengths for each respective solution in each well), rather than sequentially transporting the contents of each well into a separate sample cell of the system for analysis. For example, in particular embodiments, the well plate 1444 is mounted in a holder for controlled (by the computer 1480) translational motion of the plate in the x and y directions as shown in FIG. 14, which define a plane that is perpendicular to the beam 1432. The beam 1432 is then directed through a targeted well (and hence the contained sample) between the four vertical walls that define each well in the well plate 1444.

Any of the compensation techniques discussed above for compensating for the polarization effects of the well plate itself can be used with the system of FIG. 14 as well. Further, any of the techniques for moving the well plate 1444 relative to the system 1410 discussed above can be used with the system of FIG. 14 as well.

In the embodiment in FIG. 14, the beam source is below the well plate. Thus, the beam enters a respective well through a flat surface of the well and does not experience any meniscus effects until exiting the sample at the upper surface of the solution in the well.

As noted, the system 1410 also includes one or more meniscus-effect-mitigating components or subsystems. Examples of these components and subsystems as they are applied to the system 1410 having the beam source below the sample are discussed below with respect to FIGS. 15-21 and generally follow the examples described in FIGS. 7-13. Consequently, the discussions below are abbreviated in some instances with the understanding that they apply principles already introduced above in FIGS. 7-13 but in the context of the system of FIG. 14.

In the embodiment illustrated in FIG. 14, a PMT or APD is used in the detection subsystem 1450. In other embodiments, however, a charge-coupled device (CCD) is used in the detection subsystem. An example embodiment of such a system is shown as system 3310 in FIG. 33.

Figure 33:
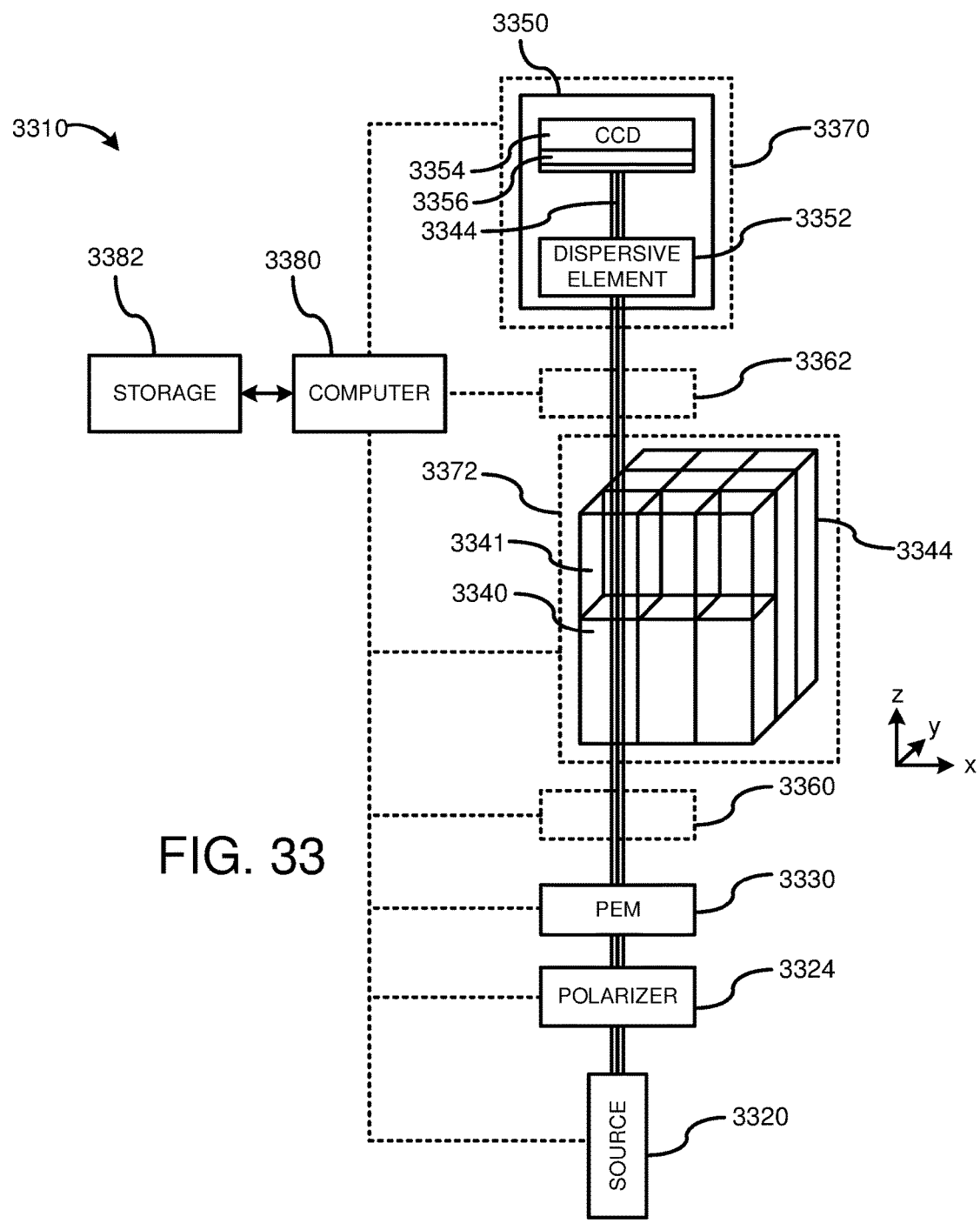

In FIG. 33, most of the elements of FIGS. 5, 6, 14, 31, and 32 are still present and have reference numerals that have been increased to the 3300s, respectively. The components related by this numbering technique (light source 3320 and PEM 3330, for example) are to be considered the same as in FIGS. 5, 6, 14, 31, and 32 unless described otherwise below. For example, the features unique to the CCD embodiments shown in FIG. 33 are the same as those shown and discussed above with respect to FIGS. 31 and 32.

In contrast to FIG. 14, the detection subsystems 3350 includes a charge-coupled device 3354 and the dispersive element (renumbered as 3352) is relocated to be part of the detection subsystem 3350 and placed in a location in front of the active region of the CCD 3354. Further, the detection subsystem 3350 can include a gain mask 3356, though in other embodiments gating or flashing of the light source 3320 is performed (as discussed above).

1. Mechanical Techniques

In some embodiments, the distance between the detection subsystem and the well plate is adjustable. FIGS. 15A-15C are cross-sectional side view illustrating the effect of such adjustments. FIG. 15A is a cross-sectional side view illustrating the case where the beam divergence caused by a meniscus 1522 prevents at least a portion of the beam from being incident on the detecting surface of the detection subsystem 1550. More specifically, FIG. 15A is a block diagram 1500 showing a cross-sectional side view of a well 1510 in a well plate containing a solution 1520 and having a vertically oriented beam 1530 incident on a bottom surface of the well 1510 and on the bottom surface of the solution 1520. In FIG. 15A the beam originates from below the well 1510 (e.g., as in the CD spectroscopy system of FIG. 14). Further, the top surface of the solution 1520 forms a concave meniscus 1522, which acts as a convergent lens for the beam 1530 when it exits the solution. In the FIG. 15A, the curvature of the meniscus 1522 is large enough such that the exiting beam has an angle of refraction that causes the focal point to be near the top surface of the solution 1520 and to then diverge in such a manner that portions of the beam are not incident on an active detection area 1551 of the detection subsystem 1550 (as illustrated by beam edges 1532, 1534). Consequently, the signal detected at the detection subsystem 1550 will be diminished and the signal-to-noise ratio reduced.

FIG. 15B is similar to FIG. 15A, but shows that the detection subsystem 1550 can be moved (e.g., translated along the z axis) downward toward the top of the well 1510. This downward translation is illustrated by arrow 1590. By doing so, the same active detection area 1551 on the detection subsystem 1550 will receive a higher percentage of the light beam 1530 interrogating the solution (and potentially all of the light beam 1530, as illustrated) than in FIG. 15A. Consequently, the signal detected at the detection subsystem 1550 can be improved and the signal-to-noise ratio increased (e.g., to its maximum possible value when adjusted to receive the entirety of the beam). The adjustable positioning of the detection subsystem 1550 can be provided through a manually adjusted mechanism (e.g., screws or pegs along a z-axis track on which the detection subsystem is mounted) or using a computer-controlled adjustment mechanism (e.g., servo-controlled or other motorized mechanism). For example, the detection subsystem 1550 can be mounted on a computer-controlled translational stage that can be automatically controlled to adjust the distance between the detector and the well plate. Further, because the solution may vary for different analysis, or for each well, the curvature of the top surface (the curvature of the meniscus) may vary and consequently its index of refraction. Accordingly, the computer-controlled mechanism can be used to provide individual adjustments for each individual well of the well plate as needed.

FIG. 15C shows a further approach to adjusting the location of the detection subsystem 1550 relative to the top of the well 1510. In FIG. 15C, the well plate including the well 1510 is moved upward toward the detection subsystem 1550. This upward translation is illustrated by arrow 1592. As in FIG. 15B, the position adjustment causes the active detection area 1551 of the detection subsystem 1550 to receive a higher percentage of the measuring light beam 730 (and potentially all of the measuring light beam 730 as illustrated), thus increasing the signal-to-noise ratio (e.g., potentially to its maximum possible value when adjusted to receive the entirety of the beam). The adjustable positioning of the well plate (and thus the well 1510) can be provided through a manually adjusted mechanism or using a computer-controlled automatic adjustment mechanism as above. Further, the adjustment mechanism can be attached to other portions of the system as well (e.g., the light source, polarizer, PEM, and/or any pre-solution lenses).

Embodiments of the disclosed technology also include systems that have both an adjustable detection subsystem (as in FIG. 15B) and an adjustable well plate (as in FIG. 15C).

Further, and as explained above with respect to FIGS. 7A-C, the shortest distance between the detector and the well plate is not always the optimized condition. For example, for certain systems, it may be desirable to have the maximum amount of the active detection surface interfacing with the beam, in which case the distance would be larger than the shortest distance. Further, as also explained above with respect to FIGS. 7A-C, in certain embodiment, the detection subsystem 1550 includes one or more apertures with varying diameters that can be either manually or computer-controlled to "clean" the measuring beam to avoid measurement artifacts, e.g., to block any portion of the beam resulting from internal reflects caused by the vertical walls of the well (as illustrated by dashed lines 436, 438 in FIG. 4).

2. Optical Techniques

In some embodiments, one or more lenses are used to reduce the effect of the sample meniscus on the resulting measurement made by the detection subsystem. As more fully explained below, one or more lenses can be located prior to the beam passing through the solution or after the beam passing through the solution.

Figure 16:
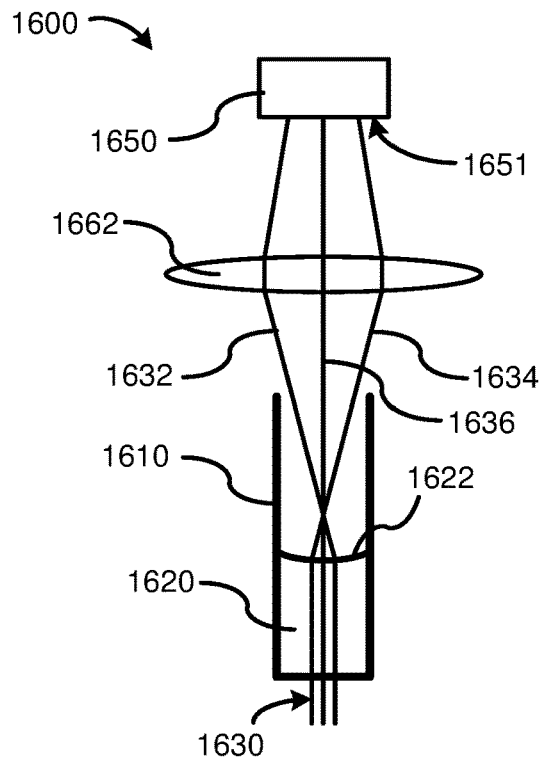
Figure 17:
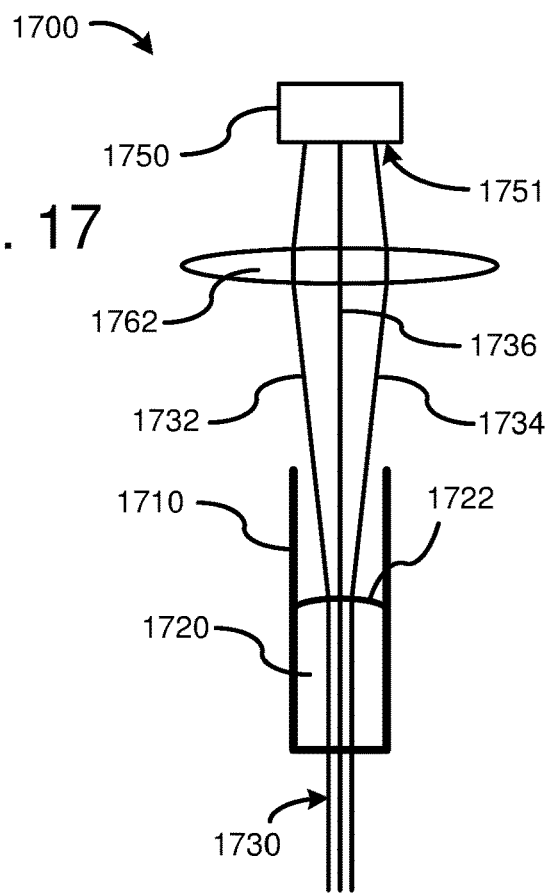

FIGS. 16 and 17 illustrate examples in which one or more lenses (illustrated as a single lens but which may actually comprise a plurality of lenses) are positioned in a location after the beam passes through the well of a well plate (e.g., a post-solution lens).

In particular, FIG. 16 is a block diagram 1600 showing a cross-sectional side view of a well 1610 containing a solution 1620 and having a vertically oriented beam 1630 incident on a bottom surface of the well 1610 and a bottom surface of the solution 1620. In FIG. 16 the beam originates from below the well 1610 (e.g., as in the CD spectroscopy system of FIG. 14). Further, the top surface of the solution 1620 forms a concave meniscus 1622, which acts as a convergent lens for the exiting beam 1630. In FIG. 16, the curvature of the meniscus 1622 is large enough such that the exiting beam 1630 refracts to create an unintended focal point above the solution and to subsequently have beam edges 1632, 1634 that diverge from a beam center point 1636. In this embodiment, a lens 1662 is positioned between the top surface of the well of the well plate and the detection subsystem 1650. The illustrated lens 1662 is a convergent lens (e.g., any suitable convergent lens) that causes the beam to converge (or at least reduces the degree of divergence in the beam). Further, the lens 1662 is located in a position (e.g., a position along the z-axis) that re-focuses the beam such that a greater percentage of the beam is incident upon an active detecting surface 1651 of the detection subsystem 1650 than in the case without the lens 1662. Accordingly, the signal at the detection subsystem 1650 can be improved and the signal-to-noise ratio increased. Further, in particular embodiments, the lens 1662 can be adjustable along the z-axis to change its focal point. For instance, the lens 1662 can be adjustable through a manually adjusted mechanism (e.g., screws or pegs along a z-axis track on which the detection subsystem is mounted) or using a computer-controlled automatic adjustment mechanism (e.g., a servo-controlled or other motorized mechanism). Further, in certain embodiments, the power of the lens itself is adjustable (e.g., by switching to a different lens with a different power (focal length)).

FIG. 17 is similar to FIG. 16 but shows the situation in which a solution 1720 in a well 1710 forms a convex meniscus 1722, which acts as a divergent lens for the exiting beam 1730. In FIG. 17, a lens 1762 is positioned between the top of the top surface of the well 1710 of the well plate and the detection subsystem 1750. The illustrated lens 1762 is a convergent lens (e.g., any suitable convergent lens) that causes the beam to converge (or at least reduces the degree of divergence in the beam). Further, the lens 1762 is located in a position (e.g., a position along the z-axis) that re-focuses the beam such that a greater percentage of the beam is incident upon an active detecting surface 1751 of the detection subsystem 1750 than in the case without the lens 1762. Accordingly, the signal at the detection subsystem 1750 can be improved and the signal-to-noise ratio increased. Further, and as explained above with respect to FIG. 16, the lens 1762 can be adjustable along the z-axis to change its focal point.

Figure 18:
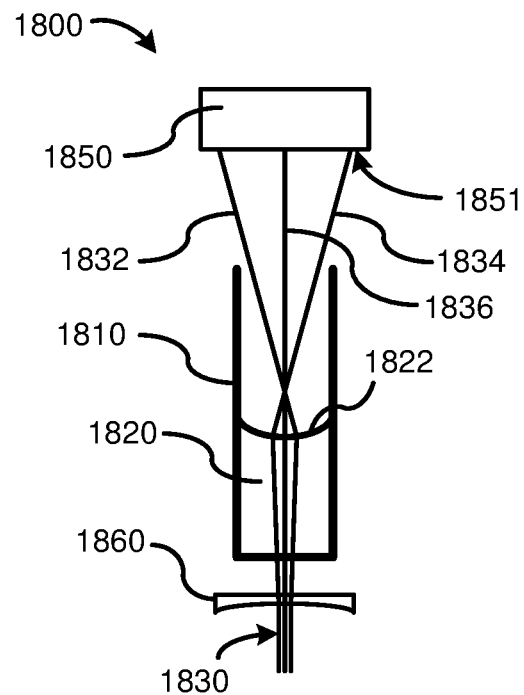
Figure 19:
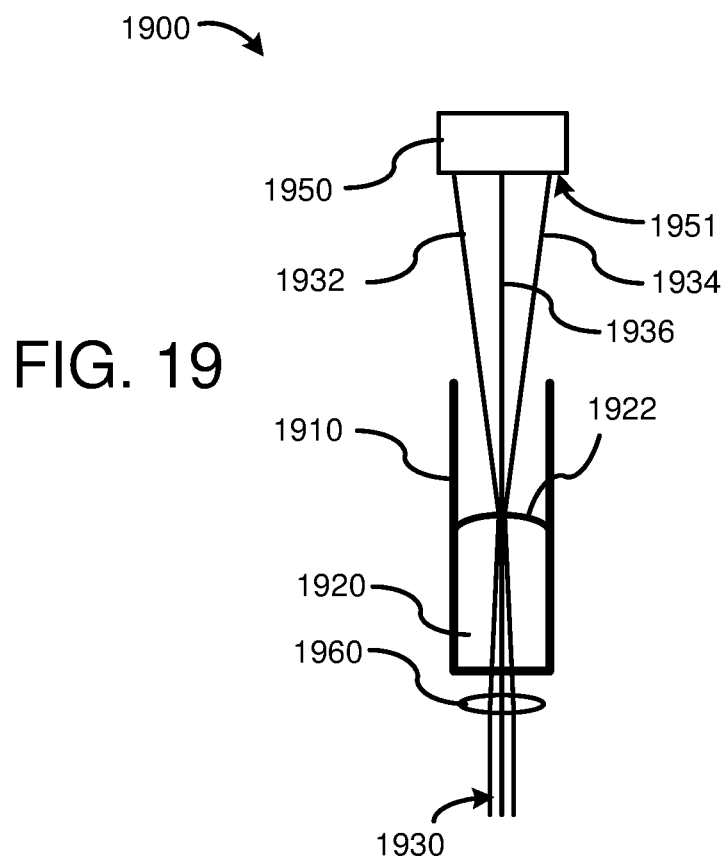

FIGS. 18 and 19 illustrate examples in which one or more lenses (illustrated as a single lens but which may actually comprise a plurality of lenses) are positioned in a location before the beam passes through the well of a well plate (e.g., a pre-solution lens).

In particular, FIG. 18 is a block diagram 1800 showing a cross-sectional side view of a well 1810 containing a solution 1820 and having a vertically oriented beam 1830 incident on a bottom surface of the well 1810 and then on bottom surface of the solution 1820. In FIG. 18 the beam originates from below the well 1810 (e.g., as in the CD spectroscopy of FIG. 14). Further, the top surface of the solution 1820 forms a concave meniscus 1822, which acts as a convergent lens for the beam 1830 as it exits the solution. In FIG. 18, the curvature of the meniscus 1822 is large enough such that the exiting beam 1830 refracts to create an unintended focal point above the top surface of well and to subsequently have beam edges 1832, 1834 that diverge from a beam center point 1836. Further, in some cases, the divergence effect caused by the meniscus 1822 can be so great that the beam edges 1832, 1834 interact with the vertical walls of the well 1810 itself in the absence of any lens (as illustrated in FIG. 1). This situation can significantly affect the quality and usefulness of the resulting measurements. In FIG. 18, a lens 1860 is positioned below the bottom of the well 1810 (e.g., between the bottom of the well plate and a PEM (not shown). The illustrated lens 1860 is a divergent lens (e.g., any suitable divergent lens) that causes the beam to diverge. Further, the lens 1860 is located in a position (e.g., a position along the z-axis) that causes the summation of the divergent effect of the lens 1860 and the convergent effect of the meniscus 1822 to result in a greater percentage of the beam being incident upon an active detecting surface 1851 of the detection subsystem 1850 than in the case without the lens 1860. Accordingly, the signal at the detection subsystem 1850 can be improved and the signal-to-noise ratio increased. Further, in particular embodiments, the lens 1860 can be adjustable along the z-axis. For instance, the lens 1860 can be adjustable through a manually adjusted mechanism (e.g., screws or pegs along a z-axis track on which the detection subsystem 850 is mounted) or using a computer-controlled automatic adjustment mechanism (e.g., a servo-controlled or other motorized mechanism). Further, in certain embodiments, the power of the lens itself is adjustable (e.g., by switching to a different lens with a different power (focal length)).

FIG. 19 is similar to FIG. 18 but shows the situation in which a solution 1920 in a well 1910 forms a convex meniscus 1922, which acts as a divergent lens for the exiting beam 1930. In FIG. 19, a lens 1960 is positioned between the bottom of the well plate and the detection subsystem 1950. The illustrated lens 1960 is a convergent lens (e.g., any suitable convergent lens) that causes the beam to converge (or at least reduces the degree of divergence in the beam). Further, the lens 1960 is positioned below the bottom of the well 1910 (e.g., between the bottom of the well plate and a PEM (not shown). The illustrated lens 1960 is a convergent lens (e.g., any suitable convergent lens) that causes the beam to converge. Further, the lens 1960 is located in a position (e.g., a position along the z-axis) that causes the summation of the convergent effect of the lens 1960 and the divergent effect of the meniscus 1922 to result in a greater percentage of the beam being incident upon an active detecting surface 1951 of the detection subsystem 1950 than in the case without the lens 1960. Accordingly, the signal at the detection subsystem 1950 can be improved and the signal-to-noise ratio increased. Further, in particular embodiments and as explained above with respect to FIG. 19, the lens 1960 can be adjustable along the z-axis.

FIGS. 20 and 21 illustrate examples in which a first set of one or more lenses (illustrated as a single lens but which may actually comprise a plurality of lenses) are positioned in a location before the beam passes through the well of a well plate, and a second set of one or more lenses (illustrated as a single lens but which may actually comprise a plurality of lenses) are positioned in a location after the beam passes through the well of a well plate.

In particular, FIG. 20 is a block diagram 2000 showing a cross-sectional side view of a well 2010 containing a solution 2020 and having a vertically oriented beam 2030 incident on a bottom surface of the well 2010 and then on the bottom surface of the solution 2020. In FIG. 20 the beam originates from below the well 2010 (e.g., as in the CD spectroscopy system of FIG. 14.). Further, the top surface of the solution 2020 forms a concave meniscus 2022, which acts as a convergent lens for the beam 2030 as it exits the solution 2020. In FIG. 20, the curvature of the meniscus 2022 is large enough such that the exiting beam 2030 refracts to create an unintended focal point above the top of the solution 2020 and to subsequently have beam edges 2032, 2034 that diverge from a beam center point 2036. A first pre-solution lens 2060 is positioned below the bottom of the well plate (e.g., between the bottom of the well plate and a PEM (not shown)). The illustrated pre-solution lens 2060 is a divergent lens (e.g., any suitable divergent lens) that causes the beam to diverge. A second post-solution lens 2062 is positioned above the top surface of the solution 2020 (e.g., between the top of the well plate and an active detecting surface of detection subsystem 2050). The illustrated post-solution lens 2060 is a convergent lens (e.g., any suitable convergent lens) that causes the beam to converge. Further, the pre-solution lens 2060 and the post-solution lens 2062 are located in positions (e.g., respective positions along the z-axis) that cause the summation of the divergent effect of the pre-solution lens 2060, the convergent effect of the meniscus 2022, and the convergent effect of the post-solution lens 2060 to result in a greater percentage of the beam being incident upon an active detecting surface 2051 of the detection subsystem 2050 than in the case without the lenses 2060, 2062. Accordingly, the signal at the detection subsystem 2050 can be improved and the signal-to-noise ratio increased. Further, in particular embodiments, either one or both of the lenses 2060, 2062 can be adjustable along the z-axis. For instance, either one or both of the lenses 2060, 2062 can be adjustable through a manually adjusted mechanism (e.g., screws or pegs along a z-axis track on which the detection subsystem is mounted) or using a computer-controlled automatic adjustment mechanism (e.g., a servo-controlled or other motorized mechanism).

FIG. 21 is similar to FIG. 20 but shows the situation in which a solution 2120 in a well 2110 forms a convex meniscus 2022, which acts as a divergent lens for the beam 2030 as it exits the solution 2120. In FIG. 21, a first pre-solution lens 2160 is positioned before the beam passes through the solution (as above in FIG. 20) and a second post-solution lens 2062 is positioned after the beam passes through the solution (as above in FIG. 20.) The illustrated pre-solution lens 2160 is a convergent lens (e.g., any suitable convergent lens) that causes the beam to converge, and the post-solution lens 2162 is a divergent lens (e.g., any suitable divergent lens). Further, the lenses 2160, 2162 are located in respective positions (e.g., a positions along the z-axis) that cause the summation of the convergent effect of the lens 2160, the divergent effect of the meniscus 2122, and the convergent effect of the lens 2162 to result in a greater percentage of the beam being incident upon an active detecting surface 2151 of the detection subsystem 2150 than in the case without the lenses 2160, 2162. Accordingly, the signal at the detection subsystem 2150 can be improved and the signal-to-noise ratio increased. Further, in particular embodiments and as explained above with respect to FIG. 20, one or more both of the lenses 2160, 2162 can be adjustable along the z-axis.

E. Well Plate Covers

Figure 22:
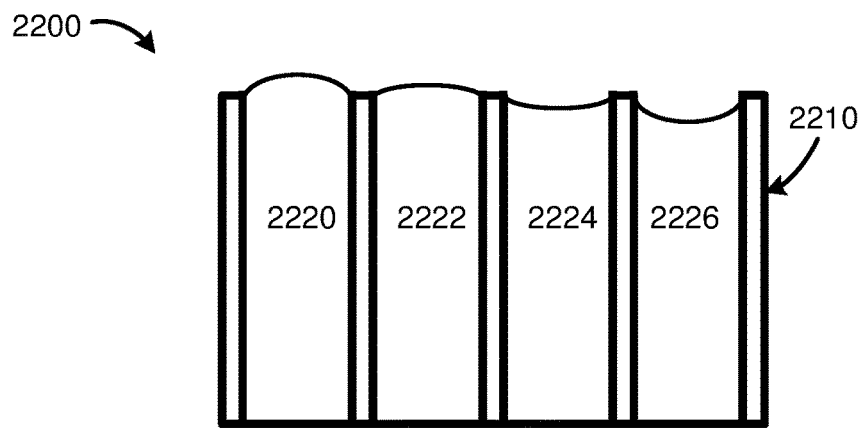
FIG. 22 is a block diagram showing various wells of a well plate filled to a top surface and having varying meniscuses.

In certain embodiments of the disclosed technology, well plate covers are used to effectively remove the meniscus at the surface of the solution being measured. For example, for solutions that form convex meniscuses, the wells of the well plate can initially be overfilled such that convex meniscuses form at the top surface of the well and extend above the x-y plane of the top surface of the well plate. This is illustrated by solution-filled wells 2220, 2222 in FIG. 22. In particular, FIG. 22 is a cross sectional side view 2200 of four representative solution-fills wells 2220, 2222, 2224, 2226 of a well plate 2210. Wells 2220, 2222 are filled with solutions having convex meniscuses, whereas wells 2224, 2226 are filled with solutions having concave meniscuses.

Figure 23:
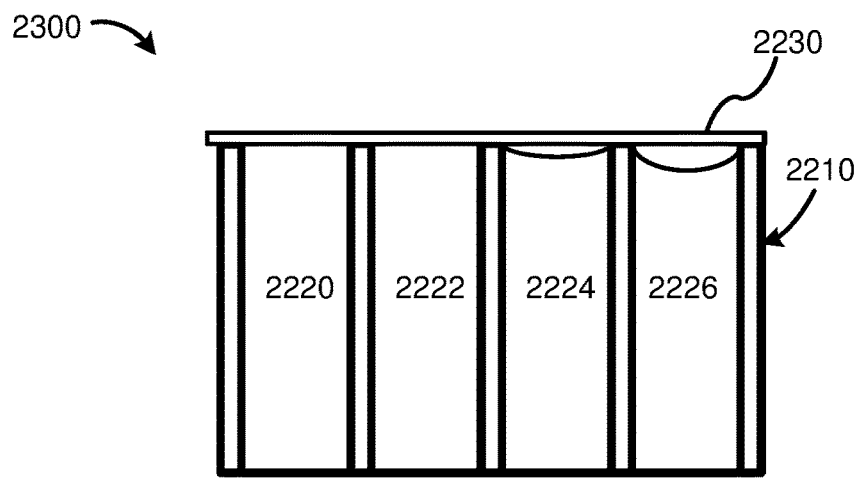
FIG. 23 illustrates a first well plate cover that can be used to reduce the meniscus effects illustrated in FIG. 22.

A translucent cover (e.g., a thin flat glass sheet) is then placed or affixed to the top surface of the well plate. This is illustrated by FIG. 23. In particular, FIG. 23 is a cross sectional side view 2300 of the four representative wells 2220, 2222, 2224, 2226 of the well plate 2210 with a flat translucent cover 2230 (e.g., a glass cover) placed on the wells.

The translucent cover 2230 then acts to remove the meniscus by compressing the solution into the well (though spillage into adjacent wells is desirably avoided during the process of mounting the cover). As illustrated, upon placement of the cover 2230, the wells 2220, 2222 in FIG. 23 no longer have any meniscus and instead have a flat top surface of the solution in each well. The flat top surface as well as the flat bottom surface allow a vertically oriented beam to pass through the solution without divergence or convergence effects caused by the meniscus. In such embodiments, any deleterious polarimetric information caused by the cover plate may be compensated for by obtaining baseline measurements with the cover in place, but with empty wells.

The use of a cover for the well plate may not work for situations in which the solution forms a concave meniscus. This is illustrated by wells 2224, 2226 in FIG. 22. In these situations, the meniscus will still be present when the flat cover is placed on top of the well plate. This is illustrated in FIG. 23 by wells 2224, 2226. Further, for all cases (2220 to 2226), there is a possibility that an air bubble is trapped under the cover. The air bubble potentially creates an even stronger curvature of the solution, acting as an even stronger lens to refract the measuring light beam.

Figure 24:
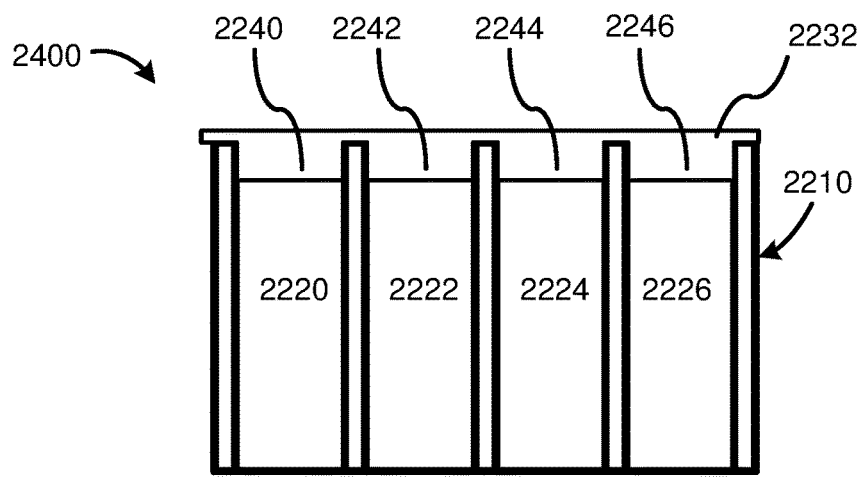
FIG. 24 illustrates a second well plate cover that can be used to reduce the meniscus effects illustrated in FIG. 22.

In other embodiments, one or more translucent plugs are used to cap the top of the wells of the well plate. For example, a glass plate having glass plugs sized to the diameter of each respective well and positioned along the glass plate at a location that allows the plugs to be inserted into each well can be used. Alternatively, the plugs can be separate plugs for each respective well. By using plugs, well plates and solution combinations that create concave meniscuses can, in some cases, be accounted for. This is illustrated by cross-sectional side view 2400 in FIG. 24, which shows the wells 2220, 2222, 2224, 2226 being "capped" by a glass plate 2232 having respective plugs 2240, 2242, 2242, 2246 attached therefore and for insertion into the well. In this case, the wells may not need to be overfilled, thus reducing the potential for cross-contamination between wells caused by spillage when the cover is placed.

F. Further Embodiments

Figure 25:
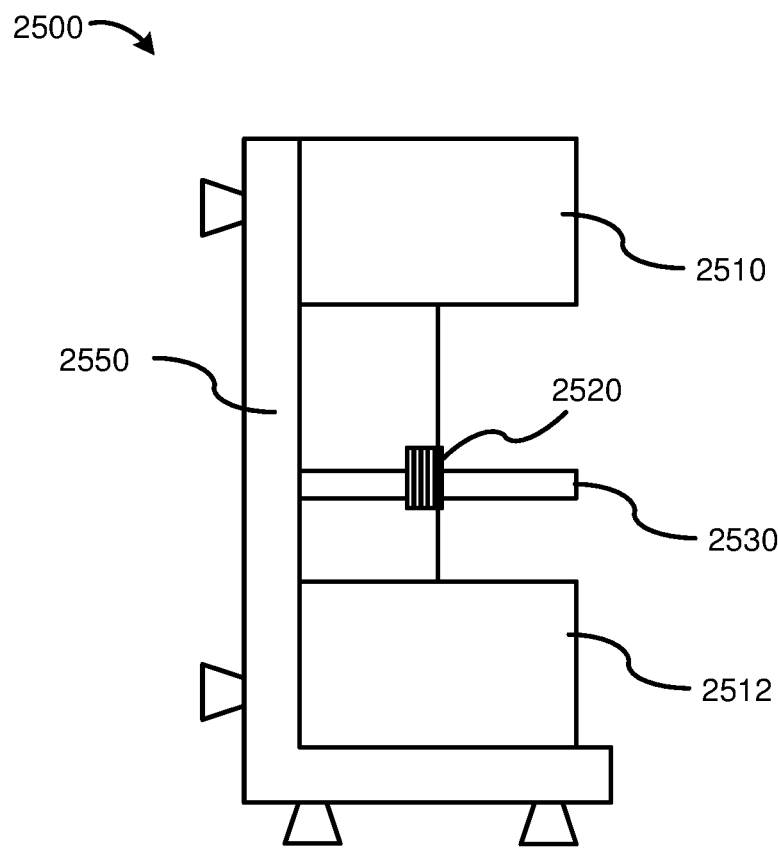
FIGS. 25 and 26 illustrate an embodiment of a system that can perform spectroscopy with a vertically oriented beam as well as a horizontally oriented beam.
Figure 26:
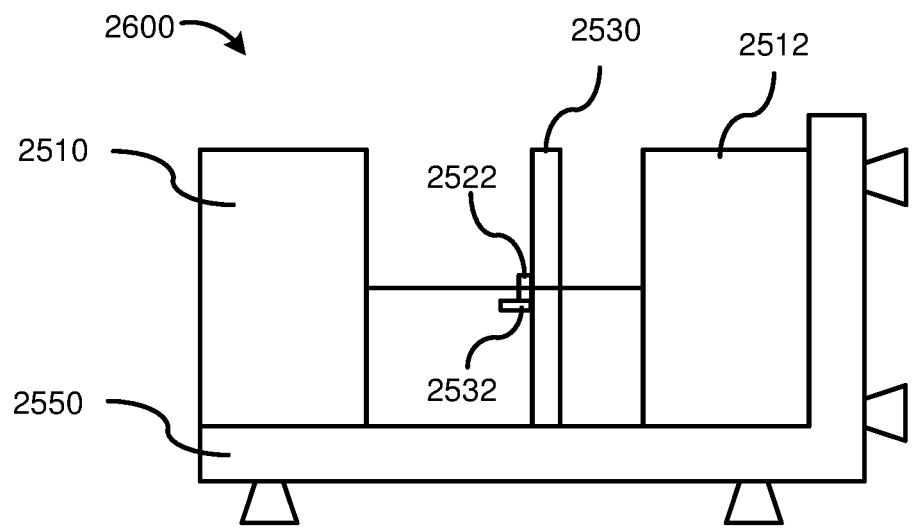

In certain embodiments, the spectroscopy system is reconfigurable to allow for both vertical and horizontal beam orientations. FIGS. 25 and 26 are schematic block diagrams 2500, 2600 illustrating one embodiment of such a system. In FIG. 25, in a vertically-oriented beam system, the pre-solution components are shown as source module 2510 and the post-solution components are shown as detector module 2512. The source module 2510 and detector module 2512 can include any of the meniscus-mitigating components discussed herein. Also shown in FIG. 25 is an x-y translation stage 2530 to which a well plate 2520 is coupled. The modules 2510, 2512, and stage 2530 in this embodiment are affixed to an L-shaped frame 2550.

As shown in FIG. 26, the L-shaped frame 2550 allows the system to be re-configured as a spectroscopy system having a horizontally oriented beam. The L-shaped frame 2550 is rotated to form a horizontal beam system. The sample can be adjusted for this orientation by using an attachment 2532 to the x-y translation stage that creates a movable platform for the still-vertical sample 2522. Further, in this embodiment, the sample 2522 may be a well plate having only one column (or one row) or be a single sample cell in order to allow for the beam to pass through only a single well (or cell) at a time.

Further, in both FIGS. 25 and 26 it is understood that the x-y translation stage holds the well plate in a manner that allows the translation stage to not interfere with the measurement itself (e.g., by holding the well plate at its edges or having a translucent (e.g., glass) portion that allows passage of the measurement beam). Also, although the embodiment is illustrated with the beam originating from above the sample, the system can include a source beam that originates from below the sample.

Still further, the components can be mounted on a C-shaped frame that allows for the entire system to be rotated 180 degrees, thus changing the orientation from a source-beam-on-top system to a source-beam-on-bottom system. Other mechanisms for altering the source beam location are also possible, such as mounting the components on a rotatable frame that rotates about a center point that is then affixed to a stationary frame or housing.

Figure 27:
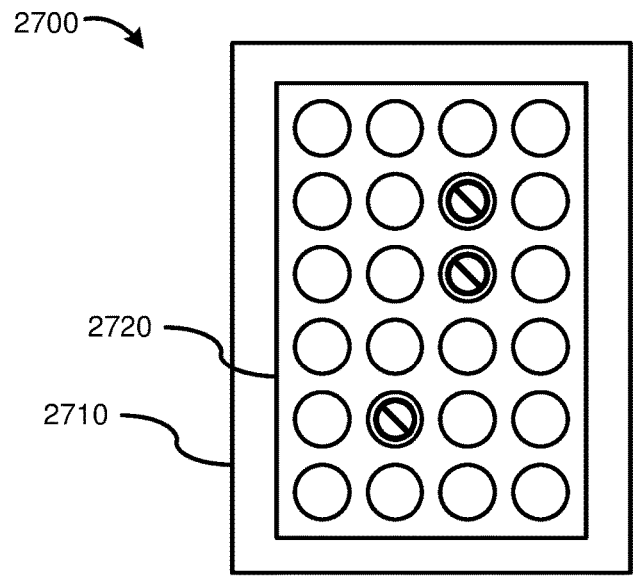
FIGS. 27-30 illustrate various techniques for further increasing the speed with which spectroscopy can be performed in accordance with embodiments of the disclosed technology.

Embodiments of the disclosed technology also include various further mechanisms for improving the speed with which spectroscopy measurements can be taken. For example, the computer-controlled x-y translational stage can be programmed to de-select or "skip" certain wells because they are unnecessary to be analyzed. FIG. 27 is a block diagram 2700 that illustrates this by showing a well plate 2720 on an x-y translational stage 2710 having several de-selected wells (shown as having cross symbols within the de-selected well).

Figure 28:
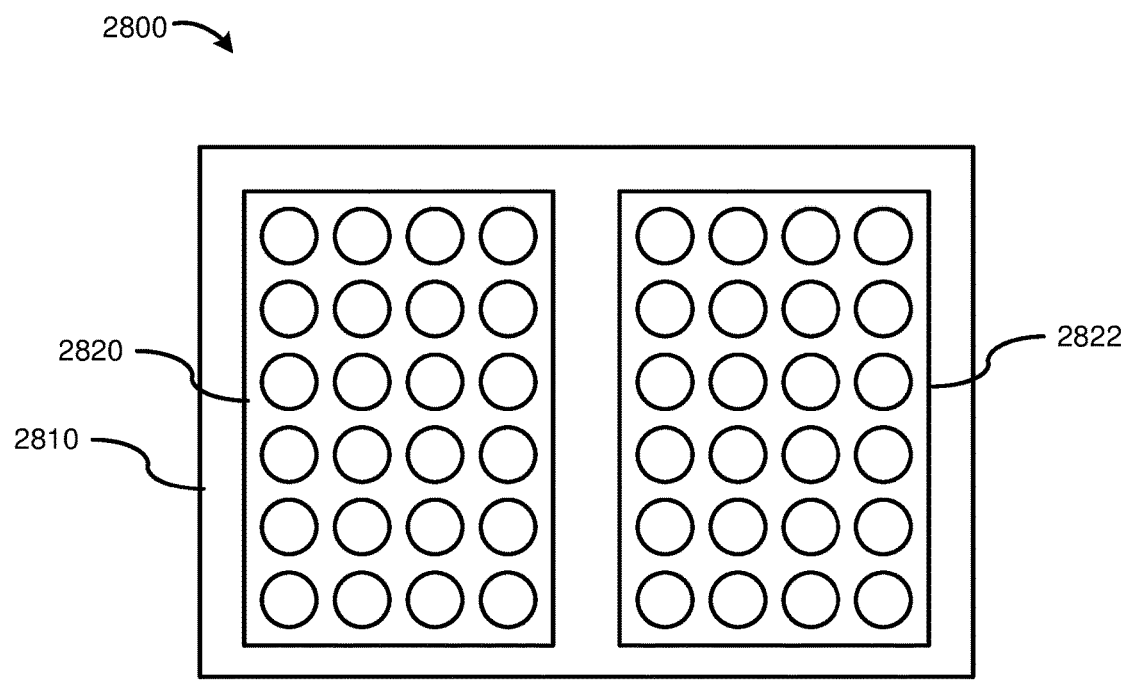
Figure 29:
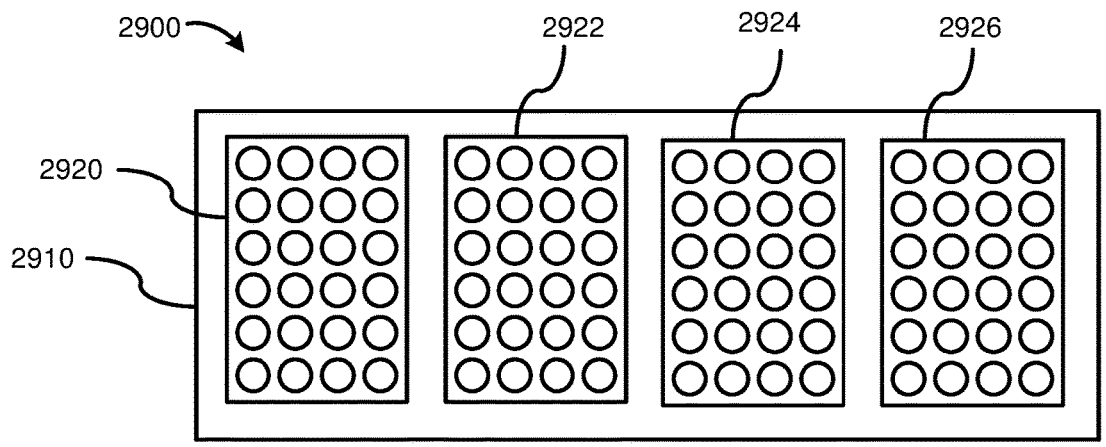
Figure 30:
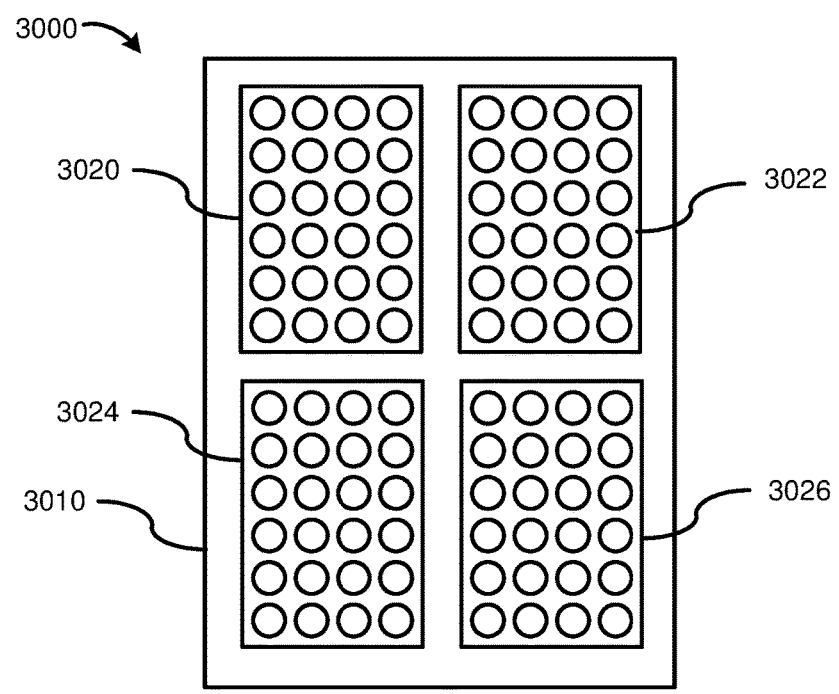

Other techniques to improve the speed of spectroscopy include the use of xy stages that are configured to hold multiple well plates. This allows for one well plate to be analyzed while another well plate is being prepared and then placed onto the stage before the analysis of the first well plate is completed. FIG. 28 is a block diagram 2800 that illustrates an embodiment of an x-y stage 2810 configured to have two well plates 2820 and 2822. FIG. 29 illustrates another embodiment of an x-y stage 2910 configured to have four well plates 2920, 2922, 2924, 2926 in a row. FIG. 30 illustrates another embodiment of an x-y stage 3000 configured to have four well plates 3020, 3022, 3024, 3026 arranged in a rectangular fashion. Likewise, multiple well plates awaiting analysis could be stacked on top of one another, in a cassette-loading assembly.

The stage configured to contain the well plates can also have different shapes and movement capabilities. For instance, in certain implementations, the stage is circular and includes two or more locations for well plates. In such embodiments, the well plate on one side of the circular stage can be loaded while the well plate on the other side is being scanned. The stage can then be rotated to move the newly loaded well plate into position for scanning when ready.

In further embodiments, the spectroscopy system is contained within a controlled environment. For example, the spectroscopy system (or portions of it) can be enclosed in a housing or room that is purged with a selected gas. For instance, the housing or room can be nitrogen purged in order to prevent UV absorption. Additionally, the housing or room can be temperature controlled to prevent any measurement anomalies caused by temperature differences.

G. Concluding Remarks

Having illustrated and described the principles of the disclosed technology, it will be apparent to those skilled in the art that the disclosed embodiments can be modified in arrangement and detail without departing from such principles. For example, any one or more aspects of the disclosed technology can be applied in other embodiments. In view of the many possible embodiments to which the principles of the disclosed technologies can be applied, it should be recognized that the illustrated embodiments are only preferred examples of the technologies and should not be taken as limiting the scope of the invention.

What is claimed is:

1. A method for measuring a polarimetric parameter of a liquid sample, comprising:
    directing a light beam of polarization modulated light along a vertical path through a first lens and a second lens and through the liquid sample, thereby producing a light beam that emanates from the sample, the liquid sample having a meniscus formed at a top surface of the sample that refracts the light beam;
    detecting the emanating light beam at a detection surface of a photomultiplier tube, avalanche photodiode, or charge-coupled device; and
    adjusting a vertical distance between the detection surface and the liquid sample to increase an amount of the emanating light beam that is incident on the detection surface and thereby compensating for the refraction caused by the meniscus of the liquid sample.

2. The method of claim 1, wherein a source for the light beam is located above the liquid sample.

3. The method of claim 1, wherein a source for the light beam is located below the liquid sample.

4. The method of claim 1, wherein the liquid sample is contained within a well of a multi-well well plate.

5. A method for measuring a polarimetric parameter of a liquid sample, comprising:
    directing a light beam of polarization modulated light along a vertical path through the liquid sample and thereby producing a light beam that emanates from the sample, the liquid sample having a meniscus formed at a top surface of the sample that refracts the light beam;
    detecting the emanating light beam at a detection surface of a photomultiplier tube, avalanche photodiode, or charge-coupled device;
    inserting a first lens along the vertical path of the light beam before the light beam passes through the liquid sample, the first lens being a convergent or divergent first lens; and
    inserting a second lens along the vertical path of the light after the light beam passes through the liquid sample, the second lens being a convergent or divergent second lens,
    the first and second lens together causing an amount of the emanating light beam that is incident on the detection surface to be increased, thereby compensating for the refraction caused by the meniscus of the liquid sample.

6. The method of claim 5, wherein a source for the light beam is located above the liquid sample.

7. The method of claim 5, wherein a source for the light beam is located below the liquid sample.

8. The method of claim 5, wherein the liquid sample is contained within a well of a multi-well well plate.

9. A system, comprising:
- a beam-generating subsystem configured to generate a polarization modulated measurement beam along a vertical beam path;
- a holder configured to hold one or more liquid samples and position a respective one of the liquid samples in the vertical beam path, thereby producing an emanating light beam for the respective one of the liquid samples as the measurement beam exits the respective one of the liquid samples, wherein at least the respective one of the liquid samples has a meniscus formed at a top surface of the liquid sample that causes refraction when the polarization modulated measurement beam passes therethrough;
- a detection subsystem configured to detect the emanating light beam; and
- one or more meniscus-effect-mitigating components positioned along the vertical beam path,
- wherein the one or more meniscus-effect-mitigating components positioned along the vertical beam path include a first lens and a second lens located before the measurement beam is transmitted through the respective one of the liquid samples, and wherein the first and second lens together cause an amount of the emanating light beam that is incident on the detection surface to be increased, thereby compensating for the refraction caused by the meniscus of the liquid sample.

10. The system of claim 9, wherein the one or more meniscus-effect-mitigating components positioned along the vertical beam path include a mechanism for adjusting the distance between the holder and the detection subsystem.

11. The system of claim 9, wherein the detection subsystem comprises a photomultiplier tube or avalanche photodiode.

12. The system of claim 9, wherein the detection subsystem comprises a charge-coupled device.

13. The system of claim 12, wherein the detection subsystem further comprises a dispersive element positioned in front of the charge-coupled device.

14. The system of claim 9, wherein the beam-generating subsystem comprises a beam source, a polarizer, and an optical polarization modulation device configured to modulate the polarization of a light beam from the beam source.

15. The system of claim 14, wherein the optical polarization modulation device is a photoelastic modulator.

16. The system of claim 14, wherein the beam-generating subsystem further comprises a dispersive element positioned between the light source and the polarizer.

* * * * *